US008128954B2

(12) United States Patent
Davis et al.

(10) Patent No.: US 8,128,954 B2
(45) Date of Patent: Mar. 6, 2012

(54) BIODEGRADABLE DRUG-POLYMER DELIVERY SYSTEM

(75) Inventors: Mark E. Davis, Pasadena, CA (US); Kenneth W. Wright, Rolling Hills Estate, CA (US); Brendan Mack, Pasedena, CA (US)

(73) Assignee: California Institute of Technology, Pasadena, CA (US)

( * ) Notice: Subject to any disclaimer, the term of this patent is extended or adjusted under 35 U.S.C. 154(b) by 1246 days.

(21) Appl. No.: 11/148,011

(22) Filed: Jun. 7, 2005

(65) Prior Publication Data
US 2005/0276841 A1 Dec. 15, 2005

Related U.S. Application Data

(60) Provisional application No. 60/577,906, filed on Jun. 7, 2004, provisional application No. 60/631,448, filed on Nov. 29, 2004.

(51) Int. Cl.
*A61F 2/00* (2006.01)

(52) U.S. Cl. .......................................................... 424/426

(58) Field of Classification Search .................. 424/426, 424/423, 422
See application file for complete search history.

(56) References Cited

U.S. PATENT DOCUMENTS

| | | | | |
|---|---|---|---|---|
| 3,642,003 | A | 2/1972 | Kurtz | |
| 3,833,002 | A | 9/1974 | Palma | |
| 3,998,988 | A | 12/1976 | Shimomai | |
| 4,274,985 | A | 6/1981 | Szejtli et al. | |
| 4,931,524 | A | 6/1990 | Sato et al. | |
| 4,946,929 | A | 8/1990 | D'Amore et al. | |
| 5,056,658 | A | 10/1991 | Sobel et al. | |
| 5,584,877 | A | 12/1996 | Miyake et al. | |
| 5,620,702 | A | 4/1997 | Podell et al. | |
| 5,660,854 | A | 8/1997 | Haynes et al. | |
| 5,688,451 | A | 11/1997 | Hutton | |
| 5,710,268 | A * | 1/1998 | Wimmer | 536/103 |
| 5,716,376 | A | 2/1998 | Roby et al. | |
| 5,889,075 | A | 3/1999 | Roby et al. | |
| 5,985,772 | A | 11/1999 | Wood et al. | |
| 6,066,170 | A | 5/2000 | Lee | |
| 6,517,759 | B1 | 2/2003 | Ferenc et al. | |
| 6,582,717 | B1 | 6/2003 | Shastri et al. | |
| 6,585,767 | B1 | 7/2003 | Holley et al. | |
| 6,596,296 | B1 * | 7/2003 | Nelson et al. | 424/426 |
| 6,673,361 | B1 | 1/2004 | Ogura et al. | |
| 6,689,378 | B1 | 2/2004 | Sun et al. | |
| 6,713,081 | B2 | 3/2004 | Robinson et al. | |
| 6,897,168 | B2 | 5/2005 | Branham et al. | |
| 2002/0055759 | A1 | 5/2002 | Shibuya | |
| 2002/0110635 | A1 | 8/2002 | Brubaker et al. | |
| 2003/0017208 | A1 * | 1/2003 | Ignatious et al. | 424/486 |
| 2003/0039689 | A1 | 2/2003 | Chen et al. | |
| 2003/0158598 | A1 * | 8/2003 | Ashton et al. | 623/1.42 |
| 2003/0175324 | A1 | 9/2003 | Robinson et al. | |
| 2004/0014660 | A1 * | 1/2004 | During et al. | 514/12 |
| 2004/0037871 | A1 | 2/2004 | Healy et al. | |
| 2004/0068293 | A1 | 4/2004 | Scalzo et al. | |
| 2004/0068294 | A1 | 4/2004 | Scalzo et al. | |
| 2005/0266077 | A1 * | 12/2005 | Royer | 424/469 |
| 2006/0024370 | A1 * | 2/2006 | Nguyen et al. | 424/484 |

FOREIGN PATENT DOCUMENTS

| | | | |
|---|---|---|---|
| EP | 0 575 976 | A1 | 6/1993 |
| EP | 0 780 129 | A2 | 6/1997 |
| EP | 1157708 | | 11/2001 |
| EP | 0647452 | | 8/2002 |
| WO | WO 99/43359 | | 9/1999 |
| WO | WO 01/76554 | A2 | 10/2001 |
| WO | WO 02/089815 | A2 | 11/2002 |
| WO | WO 03/090710 | A1 | 11/2003 |
| WO | WO 2004/022099 | A2 | 3/2004 |

OTHER PUBLICATIONS

Gao et al., "In vivo drug distribution dynamics in thermoablated and normal rabbit livers from biodegradable polymers", J Biomed Mater Res 62: 308-314, 2002.
Murillo et al., "Modulation of the cellular immune response after oral or subcutaneous immunization with microparticles containing *Brucella ovis* antigens", Journal of Controlled Release 85 (2002) 237-246.
Ogata et al., "Novel Synthesis of Inclusion Polyamides", Polymer Letters Edition, vol. 14, (1976) 459-462.
Ooya et al., "Synthesis and characterization of biodegradable polyrotaxane as a novel supramolecular-structured drug carrier", J. Biomater. Sci. Polymer Edn., vol. 8, No. 6, 437-455 (1997).
Qian et al., "Comparison of Doxorubicin Concentration Profiles in Radiofrequency-Ablated Rat Livers from Sustained- and Dual-Release PLGA Millirods", Pharmaceutical Research, vol. 21, No. 3, 394-399, 2004.
Qian et al., "Fabrication and characterization of controlled release poly(D,L-lactide-*co*-glycolide) millirods", J Biomed Mater Res 55: 512-522, 2001.
Qian et al., "Membrane-encased polymer millirods for sustained release of 5-fluorouracil", J Biomed Mater Res 61: 203-211, 2002.
Qian et al., "Combined modeling and experimental approach for the development of dual-release polymer millirods", Journal of Controlled Release 83 (2002), 427-435.
Qian et al., "Quantification of in vivo doxorubicin transport from PLGA millirods in thermoablated rat livers", Journal of Controlled Release 91 (2003), 157-166.
Quaglia et al., "Feeding liquid, non-ionic surfactant and cyclodextrin affect the properties of insulin-loaded poly(lactide-co-glycolide) microspheres prepared by spray-drying", Journal of Controlled Release 86 (2003), 267-278.

(Continued)

*Primary Examiner* — Michael G Hartley
*Assistant Examiner* — James Rogers
(74) *Attorney, Agent, or Firm* — Ropes & Gray LLP

(57) ABSTRACT

A sustained-release biodegradable polymeric drug-eluting fiber is disclosed. In some embodiments, the therapeutic drug is complexed with cyclodextrin. In certain embodiments, the polymeric component of the fiber comprises cyclodextrin. The fiber may be fabricated to provide a thread and/or suture. The fiber may be used for treatment of ocular diseases or disorders.

110 Claims, 16 Drawing Sheets

OTHER PUBLICATIONS

Salem et al., "X-Ray Computed Tomography Methods for In Vivo Evaluation of Local Drug Rlease Systems", IEE Transactions on Medical Imaging, vol. 21, No. 10, 2002.

Song et al., "Controlled release of U-86983 from double-layer biodegradable matrices: effect of additives on release mechanism and kinetics", Journal of Controlled Release 45 (1997), 177-192.

Szymanski-Exner et al., "Noninvasive Monitoring of Local Drug Release Using X-ray Computed Tomography: Optimization and In-Vitro/In Vivo Validation", Journal of Pharmaceutical Sciences, vol. 92, No. 2, 2003.

Trapani et al., "Encapsulation and release of the hypnotic agent zolpidem from biodegradable polymer microparticles containing hydroxypropyl-β-cyclodextrin", International Journal of Pharmaceutics 268 (2003), 47-57.

Baeyens et al., "Optimized Release of Dexamethasone and Gentamicin from a Soluble Ocular Insert for the Treatment of External Ophthalmic Infections," J. Control led Release 52:215-220 (1998).

Baeyens et al., "Clinical Evaluation of Bioadhesive Ophthalmic Drug Inserts (BODI) for the Treatment of External Ocular Infections in Dogs," J. Controlled Release 85:163-168 (2002).

Chang et al., "Two Clinical Trials of an Intraocular Steroid Delivery System for Cataract Surgery," Trans. Am. Oph. Soc. 97:261-279 (1999).

Deshpande et al., "Bioerodible Polymers for Ocular Drug Delivery," Crit. Rev. Ther. Drug Carrier Syst. 15:381-420 (1998).

DiColo et al., "A Study of Release Mechanisms of Different Ophthalmic Drugs from Erodible Ocular Inserts Based on Poly(Ethylen Oxide)," Eur. J. Pharm. Biopharm. 54:193-199 (2002).

Friedberg et al., "Device Drug Delivery to the Eye," Ophthalmology 98:725-732 (1991).

Friedrich et al., "Pharmacolkinetic Differences Between Ocular Inserts and Eyedrops," J. Ocul. Pharmacol. Ther. 12:5-18 (1996).

Hornof et al., "Mucoadhesive Ocular Insert Based on Thiolated Poly(Acrylic Acid): Development and In Vivo Evaluation in Humans," J. Controlled Release 89:419-428 (2003).

Jain R.A., "The Manufacturing Techniques of Various Drug Loaded Biodegradable Poly(lactide-co-glycolide) (PLGA) Devices," Biomaterials 21:2475-2490 (2000).

Loftsson et al., "The Effects of Water-Soluble Polymers on Cyclodextrins and Cyclodextrin Solubilization of Drugs," J. Drug Del. Sci. Tech. 14:35-43 (2004).

Sasaki et al., "One-Side-Coated Insert as a Unique Ophthalmic Drug Delivery System," J. Controlled Release 92:241-247 (2003).

Wadood et al., "Safety and Efficacy of a Dexamethasone Anterior Segment Drug Delivery System in Patients after Phacoemulsification," J. Cataract Refract. Surg. 30:761-768 (2004).

Yue et al., "A Novel Polymeric Chlorhexidine Delivery Device for the Treatment of Periodontal Disease," Biomaterials 25:3743-3750 (2004).

Barbolt, T.A. "Chemistry and safety of triclosan, and its use as an antimicrobial coating on Coated VICRYL* Plus Antibacterial Suture (coated polyglactin 910 suture with triclosan)" Surg. Infect. (Larchmt). 2002, 3 Suppl., S45-53.

Blanchemain et al. "Vascular PET Prostheses Surface Modification with Cyclodextrin Coating: Development of a New Drug Delivery System" Eur. J. Vasc. Endovasc. Surg., 2005, 29, 628-632.

Boccaccini et al. "Composite Surgical Sutures with Bioactive Glass Coating" J. Biomed. Mater. Res. Part B: Applied Biomaterials 2003, 67B, 618-26.

Bourlais et al. "Opthalmic Drug Delivery Systems-Recent Advances" Progress in Retinal and Eye Research, 1998, 17, 33-58.

Buchenska et al "Poly(ethylene terephthalate) yarn with antibacterial properties" Journal of Biomaterials Science Polymer Edition, 2001, 12, 55-62.

Castro et al. "Ciprofloxacin implants for bone infection. In vitro—in vivo characterization" J. Controled Release, 2003, 93, 341-54.

Chao et al. "Preparation and study on the novel solid inclusion complex of ciprofloxacin with HP-β-cyclodextrin" Spetrochimica Acta Part A, 2004, 60, 729-734.

Charoo et al. "Ophthalmic Delivery of Ciprofloxacin Hydrochloride from Different Polymer Formulations: In Vitro and In Vivo Studies" Drug Dev. Ind. Pharm. 2003, 29, 215-221.

De Rosa et al. "How cyclodextrin incorporation affects the properties of protein-loaded PLGA based microsheres: the case of insulin/hydroxypropyl-b-cyclodextrin system" J. Controlled Release, 2005, 102, 71-83.

Emerich et al. "Biocompatibility of poly (DL-lactide-co-glycolide) microspheres implanted into the brain" Cell Transplant. 1999, 8, 47-58.

Heary et al. "Drug-eluting stents: The beginning of the end of restenosis?" Cleveland Clinic Journal of Medicine, 2004, 71, 815-824.

Huang et al. "Formation of Antibiotic, Biodegradable/Bioabsorbable Polymers by Processing with Neomycin Sulfate and Its Inclusion Compound with β-Cyclodextrin" J. App. Poly. Sci., 1999, 74, 937-947.

Kato et al. "Feasibility of drug delivery to the posterior pole of the rabbit eye with an episcleral implant" Invest. Ophthalmol. Vis. Sci. 2004, 45, 238-44.

Kinane et al. "A Six-Month Comparison of Three Periodontal Local Antimicrobia Therapies in Persistent Periodontal Pockets*" J. Periodontol. 1999, 70, 1-7.

Kunou et al. "Biodegradable scleral implant for controlled intraocular delivery of betamethasone phosphate" J. Biomed. Mater. Res. 2000, 51, 635-641.

Lu et al. "Formation of Antibiotic, Biodegradeable Polymers by Processing with Irgasan DP300R (Triclosan) and Its Inclusion Compound with β-Cyclodextrin" J. App. Poly. Sci., 2001, 82, 300-309.

MacNeill et al. "Chlorhexidine Local Delivery: The Time and Ease of Placement of the Chlorhexidine Chip Local Delivery System" Compendium, 1998, 19, 1158-1167.

Nelson et al. "Technical Report: Technique for Wet-Spnning Poly(L-lactic acid) and Poly(DL-lactide-co-glycolide) Monofilament Fibers" Tissue Engineering, 2003, 9, 1323-1330.

Rajagopal et al. "Coronary Restenosis: A Review of Mechanisms and Management" The American Journal of Medicine, 2003, 115, 547-553.

Robert et al. "Comparative Review of Topical Ophthalmic Antibacterial Preparations" Drugs, 2001, 61, 175-185.

Rosner et al. "Rational Design of Contact Guiding, Neurotrophic Matrices for Peripheral Nerve Regeneration" Annals of Biomedical Engineering, 2003, 31, 1383-1401.

Rothenburger et al. "In vitro antimicrobial evaluation of Coated VICRYL* Plus Antibacterial Suture (coated polyglactin 910 with triclosan) using zone of inhibition assays" Surg. Infect. (Larchmt), 2002, 3 Suppl 1, S79-87.

Rusa et al. "Controlling the Behaviors of Biodegradeable/Bioabsorbable Polymers with Cyclodextrins" Journal of Polymers and the Environment, 2004, 12, 157-163.

Saishin et al. "Periocular Injection of Microspheres Containing PKC412 Inhibits Choroidal Neovascularization in a Porcine Model" Investigative Ophthamology & Visual Science, 2003, 44, 4989-4993.

Sinha et al. "Biodegradable Microspheres for Protein Delivery" J. Controlled Release, 2003, 90, 261-280.

Sundback et al. "Biocompatibility analysis of poly(glycerol sebacate) as a nerve guide material" Biomaterials, 2005, 26, 5454-5464.

Suwaidi et al. "Coronary Artery Stents" JAMA, 2000, 284, 1828-1836.

Van De Witte et al. "Formation of Porous Membranes for Drug Delivery Systems" J. of Controlled Release, 1993, 24, 61-78.

Verreck et al. "Preparation and physicochemical characterization of biodegradeable nerve guides containing the nerve growth agent sabeluzole" Biomaterials, 2005, 26, 1307-1315.

Wayenberg et al. "Ocular Bioerodible Minitablets as Strategy for the Management of Microbial Keratitis" Invest. Ophthalmol. Vis. Sci. 2004, 45, 3229-3233.

Yalcin et al. "Evaluation of Adjunctive Tetracycline Fiber Therapy with Scaling and Root Planing: Short-Term Clinical Results" Periodontal Clinical Investigations, 1999, 21, 23-27.

* cited by examiner

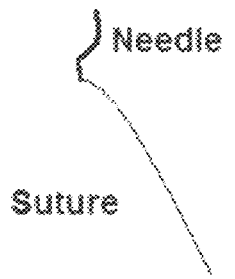
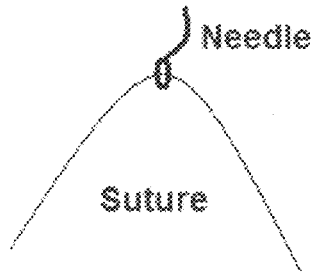
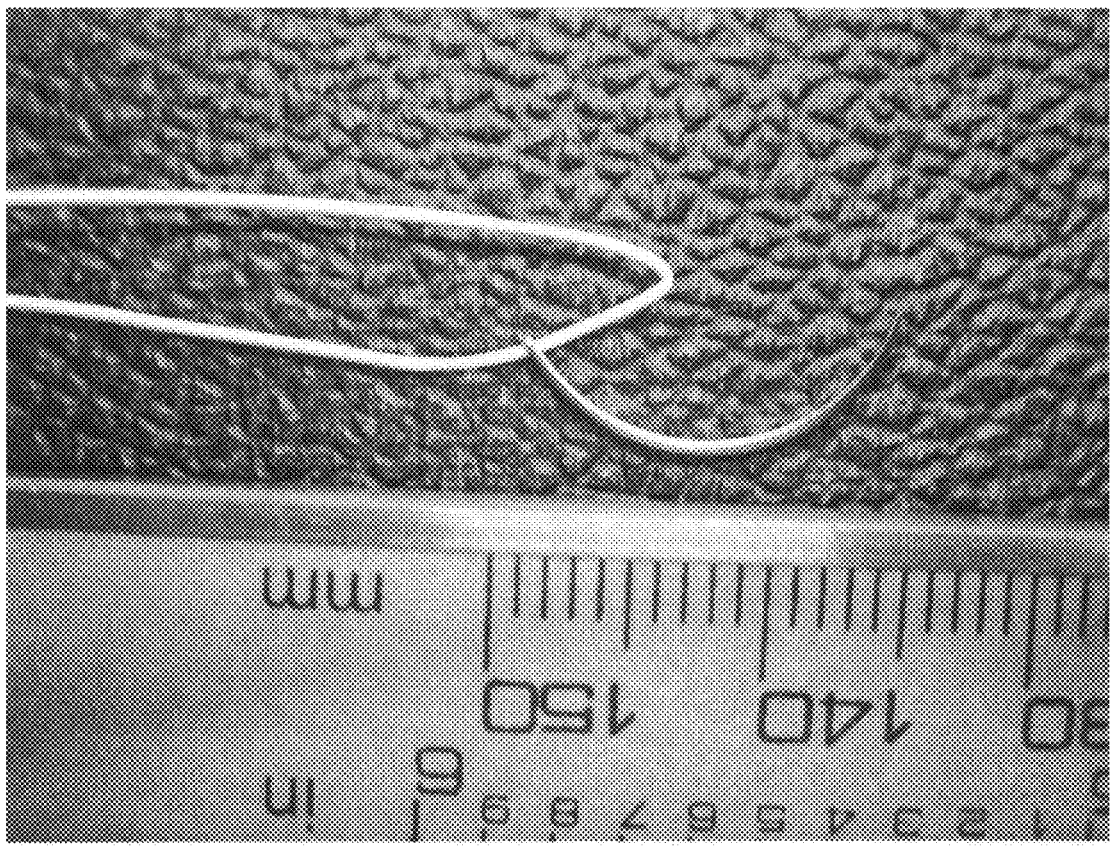
Figures 1a, 1b, and 1c. Illustrative examples of suture needle systems of the present invention.

Figures 2a and 2b. Illustrative examples of bulbs of the present invention.

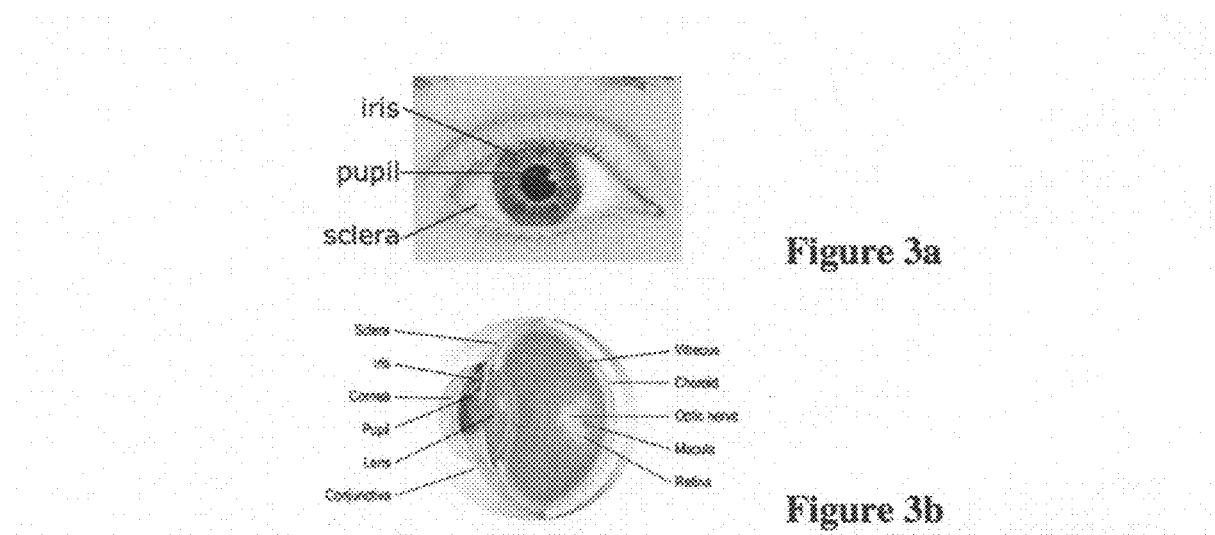
Figures 3a and 3b. Schematic illustrations of the anatomy of the eye.

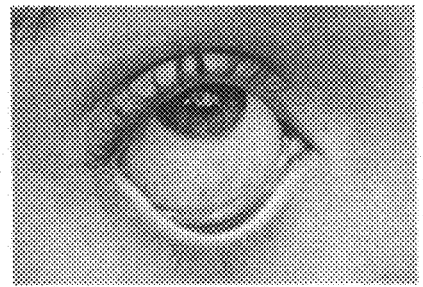
Figure 4. Photograph illustrating the lower lid conjunctival fornix.

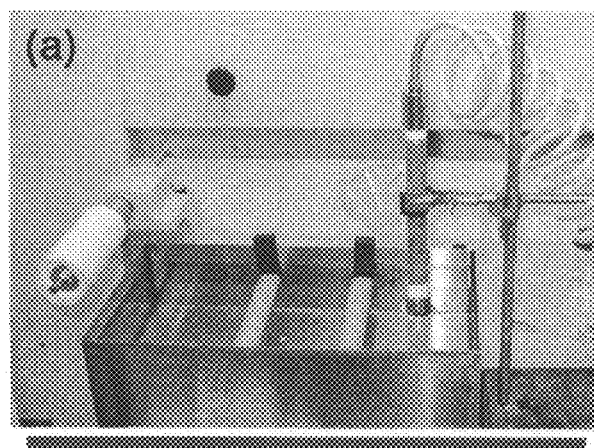
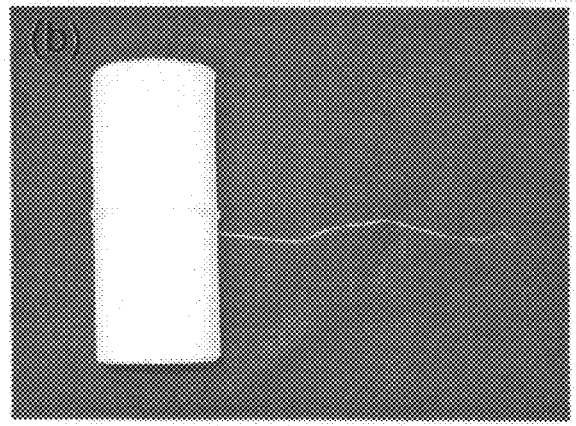
Figures 5a and 5b. Laboratory-scale wet-spinning machine constructed and employed in the instant invention. (a) The machine in the process of spinning fiber; (b) PLGA fiber spun on the take-up bobbin.

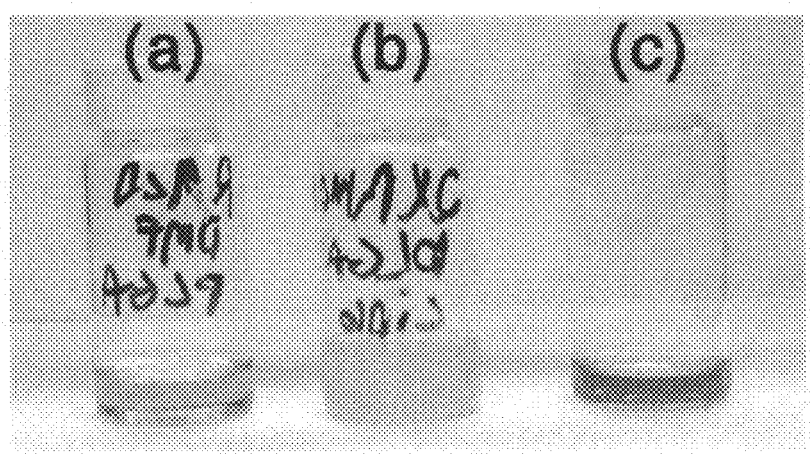

Figure 6. Solutions containing DMF and PLGA (at 33 wt%). Solution (a) is with RMβCD, (b) contains a physical mixture of RMβCD and ciprofloxacin and (c) has the inclusion complexes of RMβCD and ciprofloxacin. Note that the physical mixture is not a clear solution (mixtures of DMF, PLGA and ciprofloxacin appear like this; not shown), while the inclusion complexes are dissolving to give a clear solution.

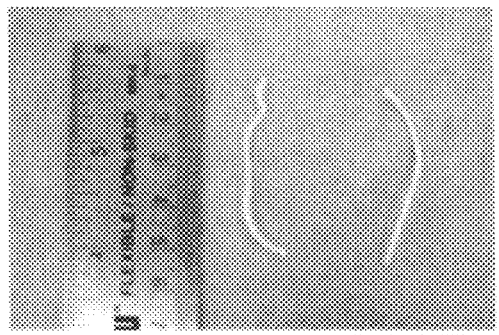
Figure 7a. Fibers of approximately 1 mm diameter. Left, PLGA; right, PLGA containing inclusion complexes of RMβCD and ciprofloxacin.
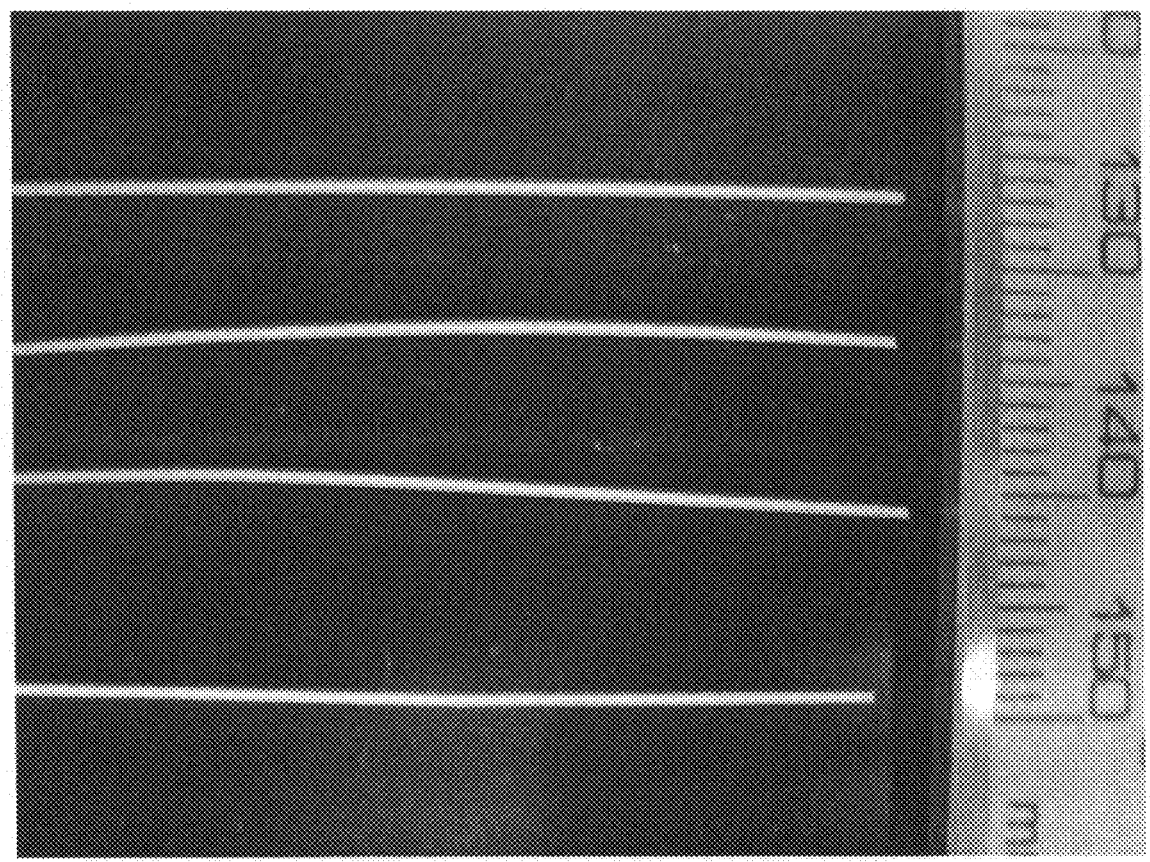
Figure 7b. Close-up view of fibers containing inclusion complexes of HPβCD and ciprofloxacin, illustrating the fiber diameter of approximately 0.4 mm.

Figure 8. PLGA fiber in bacteria plate.

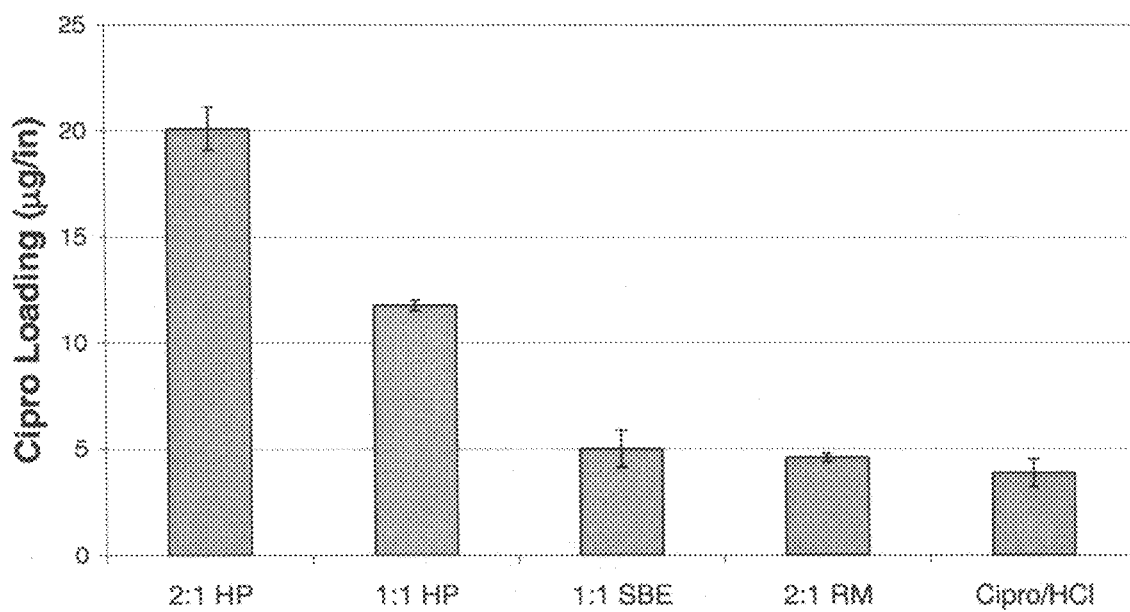
Figure 9. Drug loading levels in fibers of various formulations.

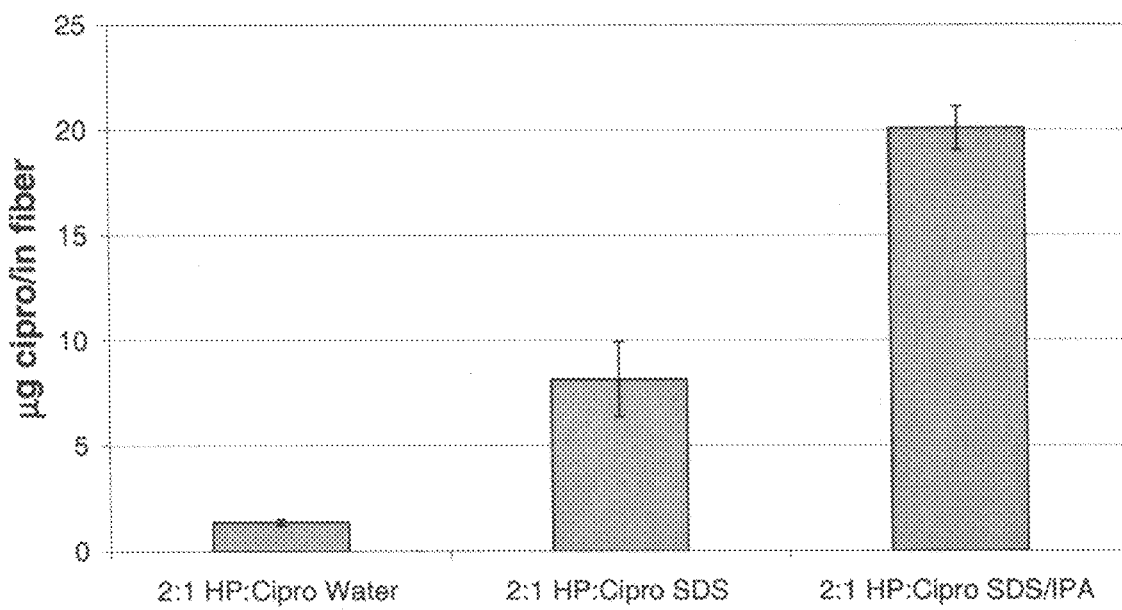
Figure 10. Drug loading levels in fibers formed from various coagulation fluids.

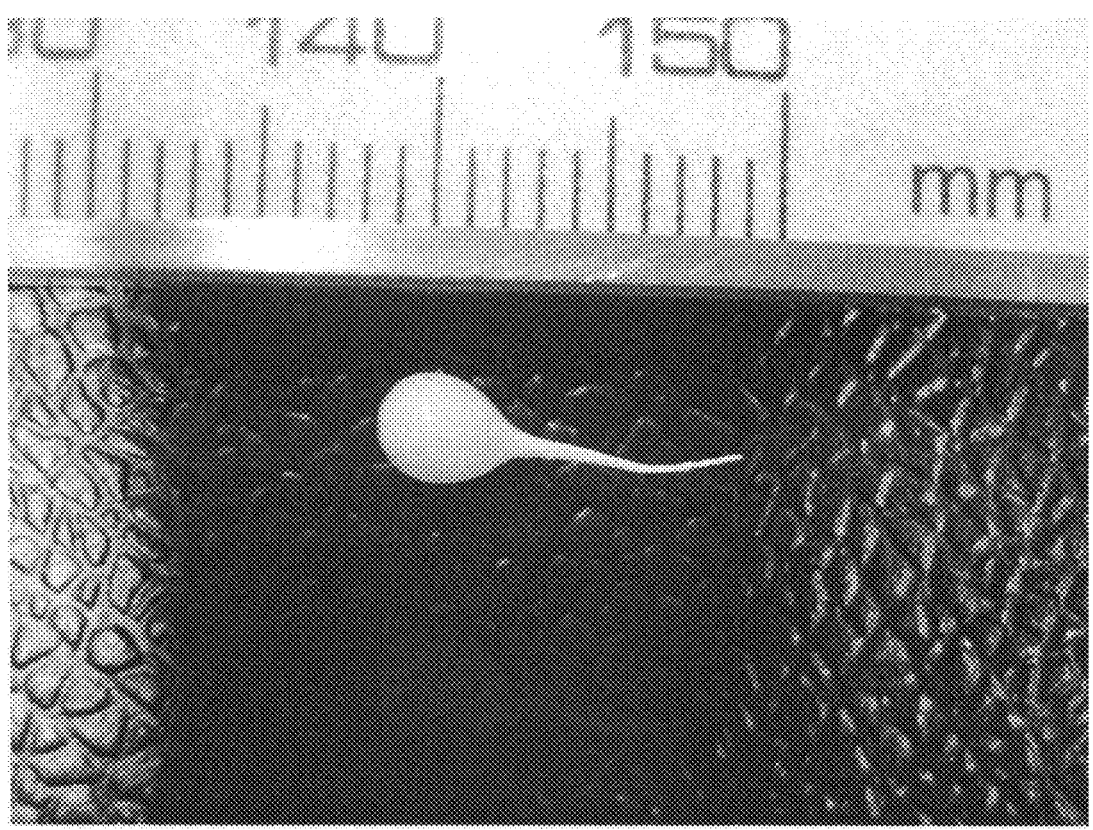
Figure 11a. Drug-eluting bulb with tail.

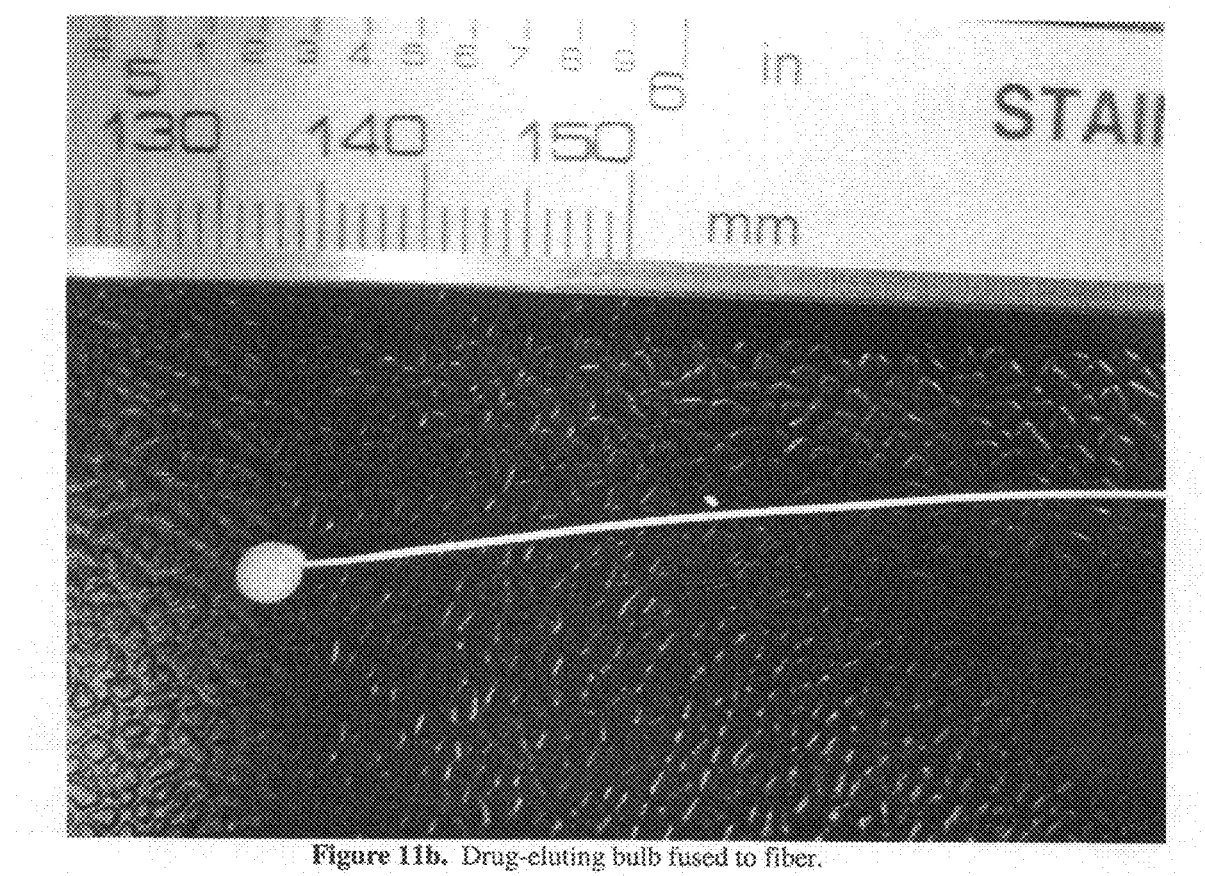
Figure 11b. Drug-eluting bulb fused to fiber.

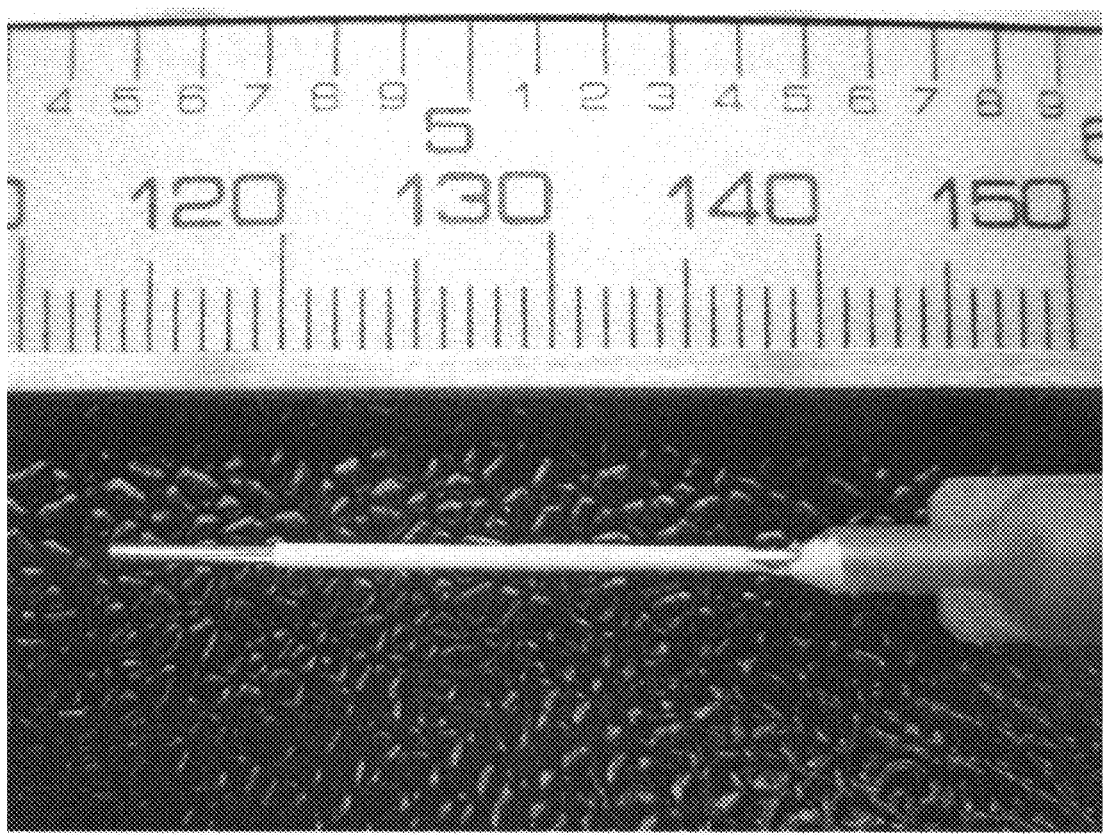
Figure 12a. Drug eluting nerve guide tube on mandrel.

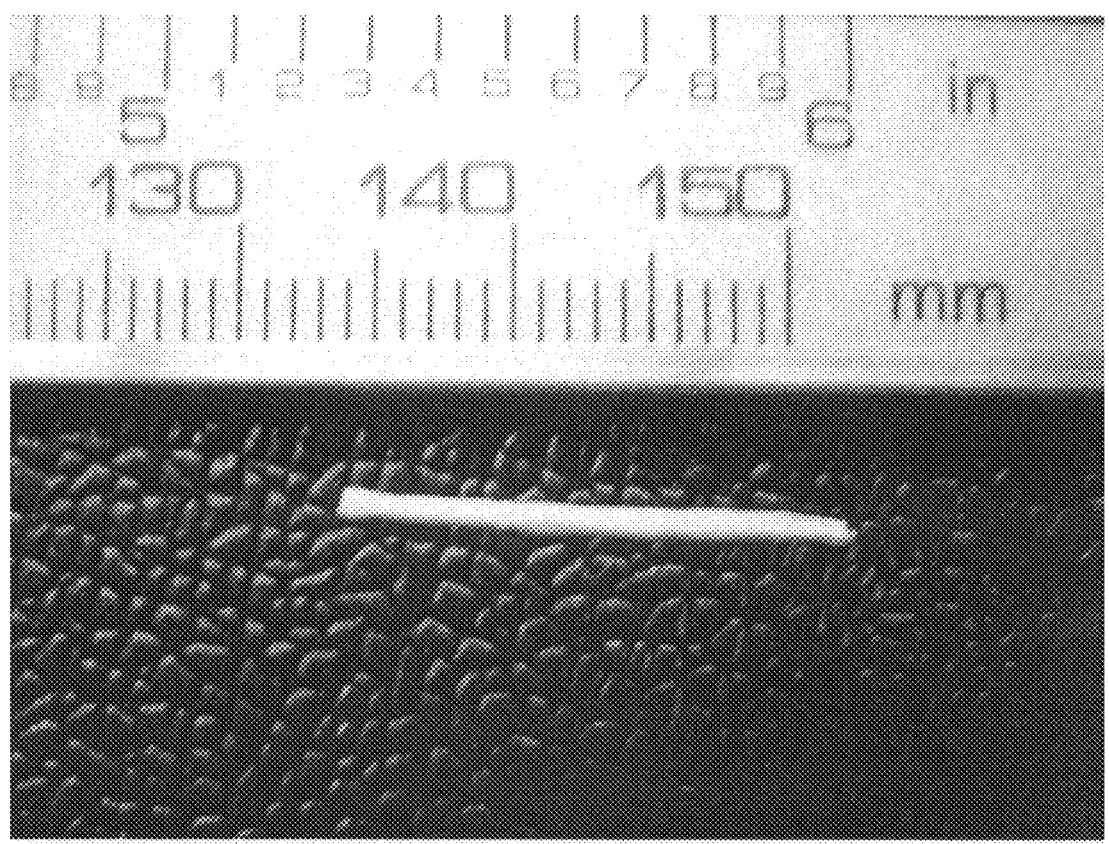
Figure 12b. Drug eluting nerve guide tube after removal from mandrel.

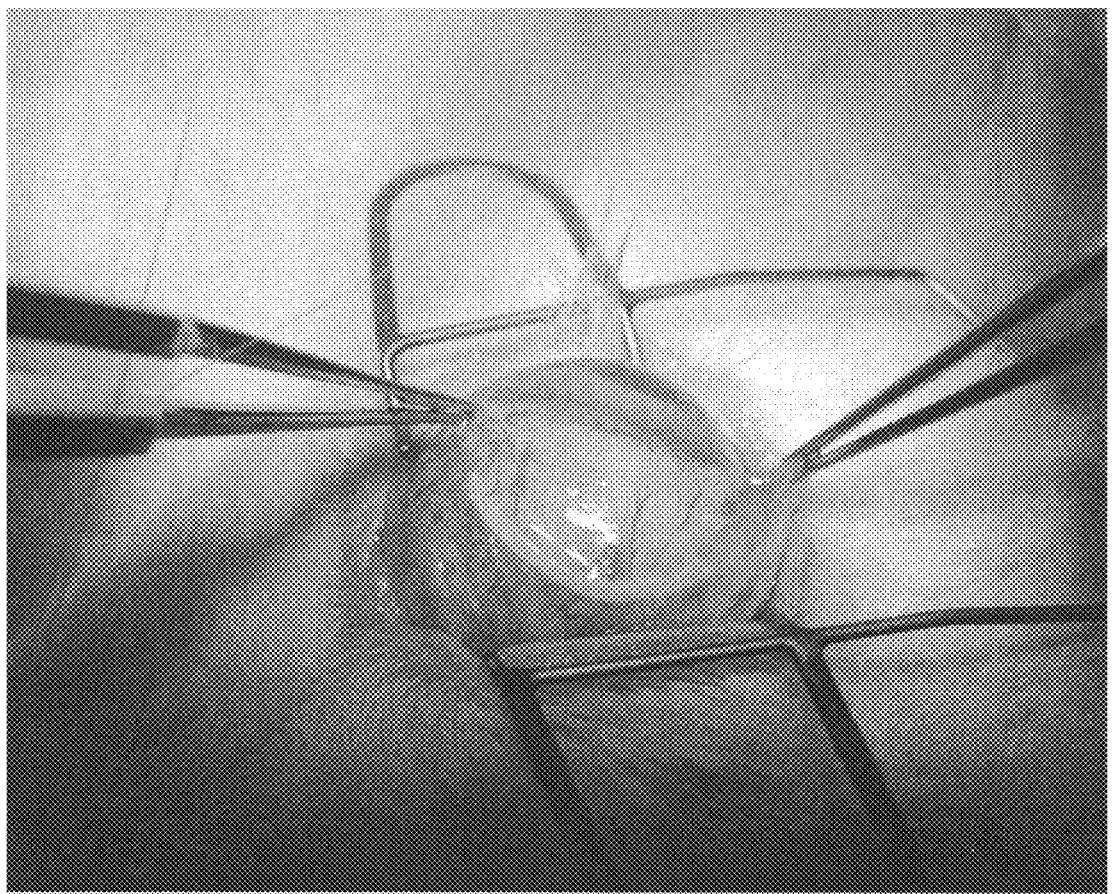
Figure 13. Photograph depicting a fiber of the present invention implanted in the eye of a rabbit.

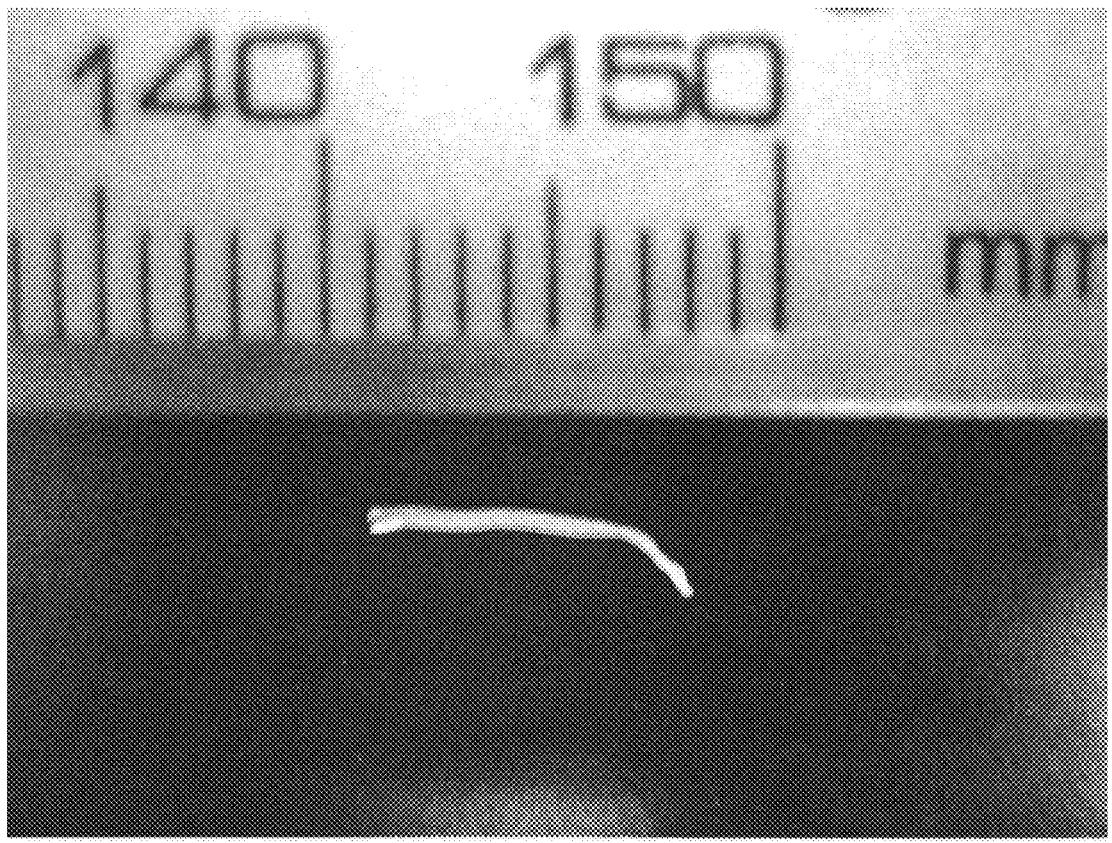
Figure 14. A double stranded suture that has been removed from an animal patient.

BIODEGRADABLE DRUG-POLYMER DELIVERY SYSTEM

RELATED APPLICATIONS

This application claims the benefit of U.S. Provisional Patent Application 60/631,448, filed Nov. 29, 2004, and U.S. Provisional Patent Application 60/577,906, filed Jun. 7, 2004, the specifications of which are incorporated by reference herein.

BACKGROUND

Numerous techniques and systems have been developed to enhance drug delivery. Principal objectives include providing therapeutically effective amounts of a drug, sustained release of a drug under conditions that allow sufficient control over the drug's delivery rate, and facile implantation of the drug delivery device.

Some systems employ a polymer drug delivery device in order to achieve such objectives. The use of controlled release polymeric systems is an approach that holds promise for improving the duration and effectiveness of drugs, for both local and systemic action. Micrometer- and nanometer-sized polymeric systems have been used to deliver precise amounts of drugs, including proteins and genes, over prolonged times to local tissues or the systemic circulation following injection. Biodegradable microparticles have been shown to be a suitable delivery vehicle. Furthermore, others have achieved sustained release by temporarily altering the chemical properties of the agent or packaging the agent with excipients or other agents with the polymer.

For polymers used as biocompatible implant materials, their properties, particularly the surface composition, are of great importance. Efforts include introducing biocompatible components into the bulk system and on their surface. Studies described, for example, in J. Colloid Interface Sci., 149:84 (1992) have shown that copolymers with a pendant glucose unit in the bulk or surfaces with covalently bound neutral polysaccharides demonstrate the reduction of platelet adhesion and protein adsorption.

Polymers having pendant sugar moieties known as "glycopolymers" (Bioconj. Chem., 3:256 (1992)) have attracted much interest in recent years, largely as scaffolds for the multivalent display of biologically important carbohydrate molecules. These glycopolymers have been used as potent inhibitors of viral-host cell attachment and leukocyte-endothelial cell adhesion (FEBS, 272:209 (1990); Can. J. Microbiol., 37:233 (1991); J. Am. Chem. Soc., 119:3161 (1997)). Glycopolymers have also been explored as vehicles for targeted drug and gene delivery (J. Hepatology, 21:806 (1994)), and as artificial substrates for cell adhesion (J. Cell Biol., 115:485 (1991)). The suitability of glycopolymers as biocompatible implant materials has been relatively unexplored and is limited to a few examples described, for example, in Microbiol. Chem. Phys., 195:3597 (1994).

Implantable surgical devices such as surgical fasteners, clips, staples, and sutures are typically employed in surgical procedures to hold body tissue together to promote the healing and joining of the tissue. Such surgical devices are often made from synthetic biodegradable or bioerodible polymers. Synthetic absorbable multifilament sutures such as Dexon, Vicryl, and Polysorb, commercially available from Davis & Geck (Danbury, Conn.), Ethicon, Inc. (Somerville, N.J.), and United States Surgical Corporation (Norwalk, Conn.), respectively, are well known in the industry. The advantage of biodegradable devices is that, once implanted, they do not need to be removed by a separate surgical operation since they are degraded and absorbed by the body. Ideally, the surgical device maintains its strength for as long as it takes the body tissues to heal. Thereafter, the device should rapidly degrade and disappear. For example, U.S. Pat. No. 5,889,075 describes a surgical suture fabricated from a copolymer containing dioxanone, trimethylene carbonate and glycolide is treated with gamma radiation to enhance bioabsorbability without adversely effecting handling properties. An example of a highly desirable polymer for use in forming biodegradable sutures is poly(glycolic acid) (PGA). Filaments extruded from PGA are bioabsorbable and biocompatible, and therefore can safely be absorbed into the body after a relatively short time period, making it unnecessary for the sutures to be removed from the patient. One example of an absorbable suture made of a PGA polymer can be found in U.S. Pat. No. 4,621,638.

Several groups have reported the fabrication of fibers with subsequent impregnation of drug by contact with drug-containing solutions (Kurtz, 1975; Chkhikvadze et al., 1991). Electrostatic spinning of drug-laden polymer fibers has been reported (Ignatious and Baldoni, 2001; Verreck et al., 2003a; Verreck et al., 2003b; Brewster et al., 2003).

Biodegradable sutures coated with drug, usually antibiotics, can deliver drug, but the thin coat only stores minimal amount of drug. Because of the thin coat, the drug coated suture elutes drug for a short period of time. In addition, after the coating is gone, residual suture remains but does not function to elute drug.

The ability to combine the benefits of drug delivery from a polymeric system with the implementation method of a biodegradable implant such as a suture, fiber, or mesh would provide an improved method for drug delivery in the medical field.

SUMMARY OF THE INVENTION

The present system relates to sustained-release biodegradable drug polymer suitable for implantation in a patient. A biodegradable polymer is combined with one or more therapeutic agents or drugs and formulated into a drug-eluting, braided or monofilament biodegradable thread or fiber. In some embodiments, the thread or fiber may have a tube-like structure or configuration, defining a hollow core. In addition to the fiber containing a drug, coatings may be employed to carry additional drug(s) and may be applied either to an individual fiber or to a multifiber thread. Threads of the instant invention may include one or more agent-containing fibers as disclosed herein.

In some embodiments, the thread or fiber may be administered using a surgical needle or other suitable device to deliver the drug contained within the fiber to a tissue targeted for treatment. The needle can create a passage through the tissue and pull the thread through the passage. In one embodiment, the thread or fiber may be used as a suture. In certain embodiments, the invention contemplates drug-eluting sutures which provide long-term sustained release of one or more therapeutic agents or drugs. The drug-containing sutures may have diameters greater than traditional sutures. In some embodiments, the instant sutures may be used to hold tissue in place, similar to traditional sutures, and have tensile strength similar to or even higher than traditional sutures. In other embodiments where the instant sutures are not used to hold tissue in place, they may have lower tensile strengths than traditional sutures. In another embodiment, multiple individual threads or sutures are connected to a common suture-needle to allow implantation of multiple individual threads with a single needle pass. Individual threads may have similar or different composition and may thus have similar or different physical properties. For example, the threads may be sized and shaped to provide multiple drugs to one or more locations, and give different durations and rates of drug delivery. The biodegradable drug thread with needle or suture system may facilitate easy, fast, controlled implantation of precise amounts of biodegradable drug material.

Implantation of the biodegradable drug thread may be reversible, as the biodegradable drug thread can easily be removed or cut out from the site of delivery. The polymeric system employed may be biocompatible and preferably biodegradable such that on prolonged implantation within the body of a patient it is absorbed and degraded by the patient producing no harmful affects. In other embodiments, the biodegradable drug polymer thread may be combined or braided with non-absorbable material. In such embodiments, the resulting thread may be used as a suture and may offer both permanent suture strength and temporary drug delivery. In one embodiment, the thread may include one or more biodegradable sections not including a drug or one or more sections of a non-absorbable material. Such a section may be placed at a tail end of the thread, where it could be readily accessed near the surface of the tissue to facilitate removal of part or the whole of the thread. Combination of a therapeutic agent or drug with a polymeric suture facilitates repair and recovery of the targeted tissue both through therapeutic treatment by the drug agent and through the suture's ability to close and stabilize wounds, such as lacerations and incisions.

The present system also affords the ability to manipulate various variables in the drug delivery process. In particular, the method of controlling the rate of drug delivery can be tuned by controlling the characteristics of the polymer/thread or fiber system, such as chemical composition, mode of fabrication, and structural design. Methods of controlling drug delivery by chemical composition include: selection of different polymer types with different rates of biodegradability, use of polymers of differing molecular weights, incorporation of various additives to the drug-polymer matrix (including cyclodextrins), and use of different drug and prodrug forms.

Elements of structural design that can be used to adjust delivery rate, amount, and duration include the incorporation of drug-polymer bulbs as reservoirs for drugs, use of surface coatings and/or multi-walled components, as well as use of a ribbon configuration. The drug polymer bulb can be delivered to desired tissue utilizing the thread and needle system and can deliver increased amounts of drug in local or systemic fashion. The bulb may be sized and shaped to facilitate entry into the tissue, for example, by being tapered in the direction of insertion. The bulb may also be sized and shaped to impede spontaneous extrusion of the bulb, for example by including bumps, ridges, barbs, etc. In some embodiments, one or more fibers are in a ribbon configuration, presenting a flexible, flat and thin profile, which can be used to adjust implant surface area and delivery time. A ribbon configuration can also serve as a drug-eluting barrier that separates tissue structures.

Many different types of biodegradable polymers are contemplated by the systems disclosed herein. For example, polymer systems comprising Dexon, Vicryl, Polysorb, as well as poly(lactide-coglycolide) (PLGA), polyglycolic acid (PGA), and polylactic acid (PLA) are all envisioned by the present invention.

One embodiment of the present system provides a biodegradable polymeric thread or fiber containing single or multiple therapeutic agents for use in the treatment of ocular diseases and disorders. The thread or fiber may be employed as a suture to provide sustained release to an ocular target of one or more therapeutic agents or drugs over the lifetime of the suture as it degrades. For example, when the drug-eluting suture is attached to a surgical needle, the needle can be used to penetrate the conjunctiva and to deliver the attached drug-eluting suture into the sub-conjunctival space. Once the biodegradable suture is implanted under the conjunctiva, the suture may be cut close to the surface of the conjunctiva, so only a small suture tail remains. In certain embodiments, the suture is placed in the conjunctival fornix (junction between the posterior eyelid and the eyeball) where it is covered by the eyelid. As the suture degrades, one or more therapeutic agents or drugs may be released into the sub-conjunctival space and into the fornix to mix with the tear film and subsequently into the eye. By placing the suture under the conjunctiva, there is no foreign body sensation, and the suture will not migrate or dislodge.

In another embodiment, the present system provides a biodegradable polymeric thread or fiber containing single or multiple therapeutic agents for use in the treatment of diseases or inflammations of the mouth, in particular those of the teeth and gums, such as gingivitis or periodontitis. In one such embodiment, the fiber or thread contains one or more drugs or agents, such as an antibiotic, and is implanted into the periodontal tissue to provide local drug delivery as the fiber or thread degrades. In some embodiments, the fiber or thread provides sustained local delivery of the agent resulting in sustained elevated agent concentrations in the crevicular fluid. In certain embodiments, the antibiotic agent is chlorhexidine, metronidazole, minocycline, or tetracycline.

In another embodiment, the present invention contemplates a drug-eluting fiber which may serve as a guide nerve tube. The fiber may have a tube-like structure or configuration with a hollow core and/or a lumen. The walls of the fiber may contain one or more therapeutic agents which may function as nerve growth inducing agents. Examples of such agents include neurotrophic factors, for example, proteins or nucleic acids which function as nerve growth factors. Other agents include small molecules, such as sabeluzole and inosine. The fiber may contain one or more carrier molecules, such as cyclodextrins, which may enhance the pharmacological properties of the nerve guide. The hollow core of the nerve guide may also contain a medium which includes one or more therapeutic agents and/or carrier molecules.

In certain embodiments, the present invention provides a stent, shunt, or other tubular device. Such devices may consist of a monolithic polymer tube, a mesh tube formed from fibers as disclosed herein, or by coating a metal, plastic, or other stent with a polymer coating as described herein.

The present invention also considers methods for the fabrication of fibers, threads, and tubes disclosed herein. In some embodiments, wet-spinning methods are employed for the preparation of the present fibers. In certain embodiments, a coagulating fluid comprising one or more solvents, such as water and an organic alcohol, such as isopropanol, may be employed. Surfactants, such as anionic surfactants like sodium dodecylsulfate, may also be employed during the fabrication process. Preparation of the agent-containing fiber may be done at ambient temperature. Formulation of the thread or fiber from the polymer may also be done at ambient temperature. The variables in the fabrication process, such as coagulation fluid, surfactant additives, and temperature, may be tuned to prepare fibers possessing desired pharmacological and physical properties.

Accordingly, the invention contemplates a fiber comprising:
- a) one or more polymers;
- b) one or more cyclodextrins; and
- c) one or more therapeutic agents.

In certain embodiments, the therapeutic agent is present throughout the width of one or more sections of the fiber. For example, the therapeutic agent may be present at a substantially uniform concentration throughout the width of one or more sections of the fiber.

In certain embodiments, the therapeutic agent forms an inclusion complex with the cyclodextrin.

In certain embodiments, the cyclodextrin and polymer are not covalently linked. In certain embodiments, the fiber comprises one or more non-cyclodextrin containing polymers, for example, in addition to a cyclodextrin containing polymer. In certain embodiments, the non-cyclodextrin containing polymer is poly(lactide-coglycolide) (PLGA).

In some embodiments, the cyclodextrin and polymer are covalently linked. In certain embodiments, the cyclodextrin is incorporated in the backbone of the polymer. In other embodiments, the cyclodextrin is borne in side chains of the polymer.

In certain embodiments, the cyclodextrin is a modified cyclodextrin. For example, the cyclodextrin may be benzylated, acylated, or alkylated. The cyclodextrin may be a methylated cyclodextrin, a hydroxypropylated cyclodextrin, or a sulfobutylether cyclodextrin.

In certain embodiments, the polymer is biodegradable. In certain embodiments, the polymer is Dexon, Vicryl, Polysorb, poly(lactide-coglycolide) (PLGA), polyglycolic acid (PGA), polylactic acid (PLA), polycaprolactone (PCL), polydioxanone (PDO), or a combination thereof. In preferred embodiments, the polymer is PLGA.

In certain embodiments, the therapeutic agent is a nucleic acid, a protein, a peptide, a small molecule, or a combination thereof. In some embodiments, the therapeutic agent is a small molecule. For example, the therapeutic agent may be a steroid, a retinoid, a NSAID, a vitamin D3 analog, a human carbonic anhydrase inhibitor, or a combination thereof. In certain embodiments, the therapeutic agent is a steroid, such as a corticosteroid, prednisolone, and/or dexamethasone. In certain embodiments, the therapeutic agent is a protein, for example, a neurotrophic factor, such as a nerve growth factor.

In certain embodiments, the therapeutic agent is an anti-cancer agent, an antibiotic agent, an anti-inflammatory agent, an immunosuppressant, an antiviral agent, an anti-proliferative agent, an antimicrobial agent, a nerve growth inducing agent, or a combination thereof. In certain embodiments, the therapeutic agent is an antibiotic agent or an anti-microbial agent, for example, chlorhexidine, metronidazole, minocycline, tetracycline, triclosan, ciprofloxacin or tobramycin.

In certain embodiments, the therapeutic agent is a nerve growth inducing agent, for example, sabeluzole or inosine.

In certain embodiments, the fiber comprises one or more adjuvants.

In certain embodiments, the therapeutic agent is covalently linked to the polymer. The therapeutic agent may be covalently linked to the polymer by one or more linking moieties. In certain embodiments, one or more linking moieties may be cleaved under physiological conditions.

In certain embodiments, the fiber comprises one or more coatings. In certain embodiments, the coating comprises one or more therapeutic agents or adjuvants.

In certain embodiments, the fiber comprises one or more bulbs along the length of the fiber. In certain embodiments, at least one bulb comprises one or more therapeutic agents.

In certain embodiments, the fiber gradually releases the therapeutic agent over a period of time after implantation in a patient. In other embodiments, the fiber releases an initial surge of the therapeutic agent after implantation in a patient. In further embodiments, the fiber releases a gradually increasing amount of the therapeutic agent over a period of time after implantation in a patient.

In certain embodiments, the fiber includes a ribbon configuration portion.

In certain embodiments, the fiber includes a tube configuration portion. For example, the fiber may include a lumen. In certain embodiments, the lumen contains a medium that includes one or more auxiliary therapeutic agents. In some embodiments, one or more auxiliary therapeutic agents is a nerve growth inducing agent.

The invention also contemplates a thread comprising one or more fibers. In certain embodiments, the thread is a monofilament. In other embodiments, the thread is a polyfilament. In certain embodiments, the thread is braided.

In certain embodiments, the thread comprises one or more fibers that are non-bioabsorbable.

In certain embodiments, at least one additional fiber of the thread comprises one or more therapeutic agents or adjuvants.

In certain embodiments, the thread comprises one or more layers or plies.

In certain embodiments, the thread is implanted in a targeted tissue of a patient. For example, the tissue may be ocular tissue or periodontal tissue or nerve tissue.

In certain embodiments, the therapeutic agent of the thread is an antibiotic or antimicrobial agent, for example, chlorhexidine, metronidazole, minocycline, triclosan, or tetracycline.

The invention also contemplates a suture comprising one or more threads or fibers. For example, the suture may comprises two or more threads or fibers. In certain embodiments, two or more threads of the suture comprise different therapeutic agents.

In certain embodiments, the suture is attached to a needle.

In certain embodiments, the suture is implanted or tied to a targeted tissue of a patient. In certain embodiments, the tissue is ocular tissue, for example, the sub-conjunctival space or the conjunctival fornix.

The invention also provides a method for delivering one or more therapeutic agents to a targeted tissue in a patient, comprising introducing a fiber to the targeted tissue, the fiber comprising
- a) one or more polymers;
- b) one or more cyclodextrins; and
- c) one or more therapeutic agents.

In certain embodiments, the fiber in the present method includes a ribbon configuration portion, a tube configuration portion, or combinations thereof.

In certain embodiments, the tissue is ocular tissue, for example, the sub-conjunctival space or the conjunctival fornix. In other embodiments, the tissue is periodontal tissue.

In certain embodiments, the introduction of the fiber is reversible.

In certain embodiments, the therapeutic agent treats cancer.

In certain embodiments, the therapeutic agent is an antibiotic agent or an anti-microbial agent, for example, chlorhexidine, metronidazole, minocycline, tetracycline, triclosan, ciprofloxacin or tobramycin.

In certain embodiments, the therapeutic agent treats an ocular disease or disorder, for example, corneal ulcer, uveitis, scleritis, glaucoma, or vernal conjunctivitis. In certain embodiments, the therapeutic agent is ciprofloxacin, 5-fluorouracil, tobramycin, dexamethasone, prednisolone, or combinations thereof.

In certain embodiments, the therapeutic agent treats periodontitis. For example the therapeutic agent may be chlorhexidine, metronidazole, minocycline, triclosan, or tetracycline.

In certain embodiments, the tissue is nerve tissue. In certain embodiments, the therapeutic agent is a neurotrophic factor. In certain embodiments, the therapeutic agent induces nerve growth.

The invention also provides a method for the treatment of periodontitis, comprising administering to a patient a fiber comprising:
  a) one or more polymers;
  b) one or more cyclodextrins; and
  c) one or more therapeutic agents.

In certain embodiments, the therapeutic agent is an antibiotic agent.

In certain embodiments, the method comprises treating the patient with scaling and/or root planing.

The invention also provides a method for the treatment of nerve damage comprising administering to a patient a fiber comprising:
  a) one or more polymers;
  b) one or more cyclodextrins; and
  c) one or more therapeutic agents.

In certain embodiments, the therapeutic agent is a neurotrophic agent.

In certain embodiments, the fiber includes a tube configuration.

The invention also provides a method for the preparation of a drug-eluting fiber comprising:
  a) dissolving one or more polymers and one or more cyclodextrin-therapeutic agent inclusion complexes in a solvent to give a polymer solution; and
  b) exposing the polymer solution to a coagulation fluid to prepare a drug-eluting fiber.

In certain embodiments, exposing the polymer solution to a coagulation fluid comprises extruding the polymer solution into a coagulation fluid. In certain embodiments, exposing the polymer solution to a coagulation fluid comprises dip-coating.

In certain embodiments, the polymer solution is homogeneous.

In certain embodiments, one or more polymers is PLGA.

In certain embodiments, the cyclodextrin is a modified cyclodextrin.

In certain embodiments, the therapeutic agent is nucleic acid, a protein, a peptide, a small molecule, or a combination thereof.

In certain embodiments, the solvent is DMF, DMSO, or combinations thereof.

In certain embodiments, the coagulation fluid is water, an alcohol, or a combination thereof. In certain embodiments, the alcohol is isopropanol. In certain embodiments, the coagulation fluid is a water:isopropanol mixture. In certain embodiments, the coagulation fluid includes a surfactant, for example, an anionic surfactant, such as sodium dodecylsulfate.

BRIEF DESCRIPTION OF THE DRAWINGS

FIGS. 1a, 1b, and 1c depict illustrative embodiments of a suture-needle system.

FIGS. 3a and 3b show schematic illustrations of the anatomy of the eye.

FIG. 4 shows a photograph illustrating the lower lid conjunctival fornix.

FIG. 5a shows the laboratory-scale wet-spinning machine constructed and employed herein in the process of spinning fiber.

FIG. 5b shows PLGA fiber spun on a take-up bobbin.

FIG. 6 shows solutions containing DMF and PLGA (at 33 wt %). Solution (a) is with RMβCD, (b) contains a physical mixture of RMβCD and ciprofloxacin and (c) has the inclusion complexes of RMβCD and ciprofloxacin.

FIG. 7a shows two fibers of approximately 1 mm diameter. Left, PLGA; right; PLGA containing inclusion complexes of RMβCD and ciprofloxacin. FIG. 7b shows a close-up view of fibers containing inclusion complexes of HPβCD and ciprofloxacin, illustrating the fiber diameter of approximately 0.4 mm.

FIG. 8 illustrates bacterial plates containing fibers.

FIG. 9 shows a chart displaying drug loading levels in fibers of various formulations.

FIG. 10 shows a chart displaying drug loading levels in fibers formed from various coagulation fluids.

FIGS. 11a and 11b show photographs depicting bulbs of the present invention.

FIGS. 12a and 12b show photographs depicting a nerve guide tube of the present invention.

FIG. 13 shows a photograph depicting a fiber of the present invention implanted in the eye of a rabbit.

FIG. 14 depicts a double stranded suture that has been removed from an animal patient.

DETAILED DESCRIPTION OF THE INVENTION

1. Overview

Figure 2A:
FIGS. 2a and 2b depict illustrative embodiments of a thread of the present invention incorporating bulb segments.

The invention relates to manufacture of a polymer drug delivery system as a fiber or thread that can be employed for introducing therapeutically effective drugs or agents to a target tissue. In certain embodiments, a biodegradable polymer combined with one or more therapeutic drugs is fabricated into a braided or monofilament implant, such as a suture. The drug-containing sutures may have diameters greater than traditional sutures. In some embodiments the instant sutures may be used to hold tissue in place, similar to traditional sutures, and have tensile strength similar to or higher than that of traditional sutures. The sutures may include components or segments of material included in traditional sutures. Such segments, may be non-absorbable. In other embodiments where the instant sutures are not intended to hold tissue in place, the sutures may have lower tensile strengths than traditional sutures.

The present sutures may be attached to a surgical needle. The needle may be used to penetrate the desired tissue and to place the attached therapeutic suture into the desired tissue for implantation. FIG. 1a, depicts an illustrative embodiment of the suture-needle system of the present invention. In some embodiments, the needle may place multiple individual threads or filaments with a single insertion step. FIG. 1b, depicts an illustrative embodiment of the suture-needle system of the present invention using more than one filament. FIG. 1c shows a photograph of a fiber threaded through a surgical needle adjacent to a ruler illustrating the millimeter dimensions of the suture-needle system. Once the biodegradable suture(s) is implanted into the desired tissue, the needle is removed, leaving the suture in the tissue for sustained drug delivery, either local or systemic. The biodegradable drug thread with needle system may facilitate easy, fast, controlled implantation of precise amounts of biodegradable drug material. Implantation of the biodegradable drug thread may be reversible, since the biodegradable drug thread can easily be removed or cut out from the site of delivery. When multiple threads or filaments are implanted, the threads may have different properties. For example, the threads may deliver different drugs for different durations and at different rates. In one embodiment, the suture may be placed through the skin to be implanted in subcutaneous tissue or through mucus membranes such as the conjunctiva to place the therapeutic suture in sub-mucosal tissue.

The drug delivery system presented permits fast, controlled drug delivery to a target tissue providing local therapy without implant migration. The thread can be implanted in or tied to specific tissues to prevent implant migration, and hence to prevent drug delivery to non-targeted tissues. Alternatively, the thread or fiber can be implanted in subcutaneous tissue to allow absorption of the drug to the blood stream for systemic delivery. As such, the fiber or thread acts as a delivery vehicle for the drug or therapeutic agent and can be adjusted to provide local and/or systemic treatment. The therapeutic agent (and/or an adjuvant) and polymer may associate by means recognized by those of skill in the art such as, for example, electrostatic interaction, hydrogen bonding, hydrophobic interaction, formation of inclusion complexes with the inclusion hosts, or covalent attachment to the polymer, e.g., by a reversible attachment such as an ester or carbonate. In certain embodiments, the therapeutic agent and/or adjuvant may be covalently attached, optionally through a reversible linkage, to a moiety that forms an inclusion complex with the inclusion hosts, e.g., cyclodextrin. The degree of association may be determined by techniques known in the art including, for example, fluorescence studies, DNA mobility studies, light scattering, electron microscopy, and will vary depending upon the therapeutic agent. As a mode of delivery, for example, a therapeutic composition of the invention containing a material of the invention and DNA may be used to aid in transfection, i.e., the uptake of DNA into an animal (e.g., human) cell. (Boussif, O. Proceedings of the National Academy of Sciences, 92:7297-7301(1995); Zanta et al. Bioconjugate Chemistry, 8:839-844 (1997)).

Use of a suture as a drug-eluting implant obviates the need for invasive surgery to implant larger drug-eluting devices, such as disc implants. In such circumstances, the present system offers improved recovery of tissues from implantation as well as reduced incidence of complications, such as tissue infection, resulting from invasive surgery.

The present systems may use a fiber or thread composed of a polymer system which incorporates one or more layers and/or plies in the body of the fiber or thread. Additionally the fiber or thread may include fibers of different polymer types interwoven, spun, tufted, or otherwise braided with the subject fibers. Alternatively, the fiber or thread may incorporate a polymer system as a monofilament. Monofilaments, braided polyfilaments, and other associations of multiple fibers are intended to be encompassed by the term "thread" as that term is used herein. Furthermore, threads of the instant invention, in addition to comprising polymeric fibers as disclosed herein, may also be formed from the interweaving of two or more fibers followed by the fusing of these fibers by a suitable method, for example by treatment with heat and/or pressure. Threads may also be formed by the interweaving of two or more fibers followed by treatment with a cross-linking agent. Similarly, fibers and/or threads of the present invention may be further woven into fabrics, for example a cloth-like fabric. Such fabrics can be formed into various shapes, such as a conical shape or a tube-like shape, which may serve as fibers or threads as described herein. In other embodiments, the fibers of the fabrics can be fused together by a suitable method, for example by treatment with heat, pressure, and/or cross-linking agents, to give a film.

In other embodiments, threads of the present invention may comprise two or more fibers, of which one or more is not a biodegradable drug-releasing fiber of the invention. For example, when a present thread is used as a suture, the suture may also comprise one or more fibers commonly used in sutures and/or capable of being used in sutures. Some non-limiting examples of such fibers include Vicryl®, Dexon®, PDS®, Maxon®, GORE-TEX®, Polysorb, poly(lactide-coglycolide) (PLGA), polyglycolic acid (PGA), polylactic acid (PLA), polycaprolactone (PCL), polydioxanone (PDO), Nylon, Dacron, Prolene, and co-polymers thereof, as well as silk, linen, catgut, and stainless steel. For example, in one embodiment, the biodegradable polymeric thread may be combined or braided with non-absorbable material. In such embodiments, when the resulting thread is used as a suture, it may offer both permanent suture strength and temporary drug delivery. In one embodiment, the thread may include one or more biodegradable sections not including a drug or one or more sections of a non-absorbable material. Such a section may be placed at a tail end of the thread, where it could be readily accessed near the surface of the tissue to facilitate removal of part or the whole of the thread.

The fibers of the present invention may be fabricated by any suitable method, for example such as by dry-spinning, wet-spinning, or dry-wet spinning, including phase separation and/or membrane formation processes. Some examples of phase separation processes that are contemplated by the present invention include thermally induced phase separation and immersion precipitation. In some embodiments, dip-coating techniques may be employed for fabrication of the present fibers. For example, fibers formed as tube structures may be formed from dip-coating methods. Dip-coating or other analogous methods may be used to coat the subject polymeric materials onto any suitable structure, including traditional medical devices, such as stents or other devices. In addition to any suitable fabrication method, combinations of such methods may be employed. In one embodiment, a fiber of the present invention is prepared by a wet spinning method. In one embodiment a drug-eluting fiber is prepared by a) dissolving one or more polymers and a cyclodextrin-therapeutic agent inclusion complex in a solvent to give a polymer solution; and b) extruding the polymer solution into a coagulation fluid to prepare a drug-eluting fiber.

In some embodiments, dissolving the polymer and the cyclodextrin-therapeutic agent complex gives a homogenous solution. In certain embodiments, the solvent is a polar organic solvent or a non-polar organic solvent. Examples of non-polar organic solvents contemplated by the invention include benzene, hexanes, pentane, toluene, diethyl ether, chloroform, ethyl acetate, THF, dioxane, and methylene chloride. In some embodiments, the polar organic solvent is protic. In other embodiments, the polar organic solvent is aprotic. Examples of protic polar solvents contemplated by the invention include water, methanol, ethanol, propanol (all isomers), butanol (all isomers), acetic acid, and formic acid. In preferred embodiments, the solvent is a polar, aprotic organic solvent, such as DME (1,2-dimethoxyethane), NMP (N-methylpyrrolidinone), acetonitrile, acetone, DMF (dimethylformamide), DMSO (dimethyl sulfoxide), nitrobenzene, pyridine, or combinations thereof, particularly DMF or DMSO.

In certain embodiments, the fiber fabrication method may employ one or more coagulation fluids, and the invention contemplates all suitable coagulation fluids. In some embodiments, the coagulation fluid may be water, a non-polar organic solvent, a polar organic solvent, such as an alcohol, or combinations thereof. Examples of alcohols suitable for use as coagulation fluids include methanol, ethanol, propanol, butanol, and pentanol. All isomeric forms of such alcohols are contemplated, for example, isopropanol, tert-butanol, n-pentanol, etc. In some embodiments, combinations of solvents may be used as coagulation fluids, such as water:isopropanol. The exact combination and ratio of solvents may be tuned to give a coagulation fluid which affords fibers of desired properties. For example, a coagulation fluid of 75:25 water:isopropanol may afford higher loading of a therapeutic agent in the fiber than a coagulation fluid of water alone.

In certain embodiments, a coagulation fluid may contain one or more suitable surfactants and/or detergents. For example, the present invention contemplates the use of anionic, cationic, non-ionic, and ampholytic surfactants. Some non-limiting examples of surfactants that may be used with the present invention include sodium dodecylsulfate (SDS), sodium cholate, sodium deoxycholate (DOC), N-lauroylsarcosine sodium salt, lauryldimethylamine-oxide (LDAO), cetyltrimethylammoniumbromide (CTAB), and bis (2-ethylhexyl)sulfosuccinate sodium salt (DOSS), particularly SDS. The type and amount of surfactant use in the coagulation fluid may be tuned to give a coagulation fluid which affords fibers of desired properties, such as increased loading of a therapeutic agent in the fiber. In some embodiments, the surfactant may be employed in a 0 to 10% solution with a coagulation fluid, for example, in an approximately 2% solution.

The temperature at which fiber or thread formation is conducted may be tuned to afford fibers of desired properties. The temperature may also be adjusted to account for the stability of one or more therapeutic agents loaded into the fiber. For example, temperatures near or slightly above ambient may be employed when using heat-sensitive therapeutic agents, such as biological agents, for example, proteins, peptides, or polynucleotides. Thermal decomposition of such agents may be avoided. Additionally, potentially harmful and/or toxic decomposition products may also be avoided. Such thermally sensitive drugs may not be compatible with systems that rely on formation of the fiber or thread by heating. As such, formation of the fiber or thread from one or more drug or agent containing polymers may be done at temperatures below 60° C., below 50° C., below 40° C., below 30° C., or below 20° C., particular such procedures are typically performed at temperatures above 0° C., 10° C., or 20° C. Thus, for example, the process can be conducted at a temperature in the range of 0-60° C., 10-50° C., 15-40° C., or 20-30° C. In some embodiments, formation of the fiber or thread may occur at ambient temperatures. Formation of the thread or fiber at ambient temperatures may facilitate the preparation of threads or fibers with consistent and reproducible drug loadings.

Examples of fiber fabrication methods suitable for use in the present invention include those described in van de Witte, et al. *J. Control. Rel.* 1993, 24, 61-78 and Nelson et al. *Tissue Engineering,* 2003, 9, 1323-1330; the entire contents of which are hereby incorporated by reference.

A drug-eluting fiber of the present system may vary in size. In some embodiments, the thread or fiber is several centimeters long and/or a few millimeters thick. In other embodiments, the thread or fiber is only a few millimeters long and/or less than a millimeter thick. The physical dimensions of the drug-eluting fiber of the present system may be tuned to achieve desired properties in drug loading, duration of drug release, and physical properties such as tensile strength and flexibility. For example, the instant fiber may be adjusted to deliver a substantially constant amount of therapeutic agent or drug over a predetermined period of time, such as a day, three days, a week, or longer. The instant fiber may also be adjusted to deliver a large initial dose of therapeutic agent and/or to taper the dose. The instant fiber may also be adjusted to provide a delay in achieving high dosage levels, i.e., a gradual increase in drug release rate up to a target dosage.

Figure 2B:
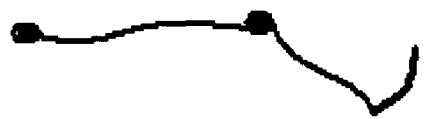

A drug-eluting thread or fiber of the present system may also employ a bulb, i.e., a thickened segment. FIGS. 2a, 11a, and 11b depict illustrative embodiments of a fiber of the present invention incorporating a bulb segment. Use of a bulb is advantageous for the implantation and delivery of large amounts of therapeutic agents or for the long-term and sustained release of an agent or drug. The bulb may serve to act as a reservoir for the agent or drug. The bulb may have a similar composition to the rest of the thread or fiber, i.e., similar construction of layers, plies, interweaves, or polymeric composition. Alternatively, the bulb may have different composition from the narrower segments of the thread or fiber system, possibly to present a different drug delivery profile. The bulb composition may or may not be biodegradable. Furthermore, the bulb segment may be used in tandem with one or more additional bulb segments, which may have similar or different properties from other bulbs and/or the remainder of the thread or fiber system. FIG. 2b depicts an illustrative embodiment of a thread or fiber of the present invention incorporating multiple bulb segments. Tandem and multiple bulb segments may increase the amount of drug that can be delivered by the thread or fiber system. In certain embodiments, a bulb may include a therapeutic agent that is not present in other portions of the fiber, and different bulbs may contain different therapeutic agents from each other. Such therapeutic agents may have complimentary properties and/or work synergistically. For example, for a suture application, the thin portions of the fiber may include a local anesthetic, while bulbs may include an antibiotic. When used in conjunction with a suture system of the invention, the bulb may be introduced into a desired location by being pulled through tissue using the needle system described herein.

An additional attribute of the bulb feature is the bulb(s) prevents migration of the thread or fiber from the site of implantation due to the larger diameter of the bulb segment versus the sites of implantation. For example, the bulb may be tapered in the direction of insertion, such as in a conical or arrow shape, to discourage retraction or spontaneous extrusion. Additionally, the bulb may also be sized and shaped to impede retraction or spontaneous extrusion, for example by including bumps, ridges, barbs, etc. In certain embodiments, the fiber or thread includes one or more surface features which permit passage of the fiber or thread in the direction of insertion/implantation, but discourage passage in the opposite direction. For example, the fiber may include one or more segments or surface portions which lie flat when the fiber is pulled in one direction, such as the direction of implantation, so as to not impede passage of the fiber through the surrounding tissue. Such segments or portions of the fiber may then flare out and/or catch or burrow into surrounding tissue when the fiber is pulled in a direction opposite to implantation, thus impeding passage and migration of the fiber in this direction. Such surface features may also be employed on a bulb section. Structural features of the thread or fiber which inhibit migration permit focused implantation of the thread or fiber and hence drug delivery system to specifically targeted tissues and may reduce delivery to non-targeted tissues.

Another aspect of the invention considers one or more ribbon configurations, wherein the fiber or thread possesses in a flexible, flat and/or thin profile or shape, which can be used to adjust implant surface area and delivery time of the drug. For example, a ribbon may have a width at least five, ten, or even twenty, thirty, one hundred or more times as great as the thickness of the ribbon. The thickness of the ribbon is typically less than 2 mm, 1 mm, 0.5 mm, or even less than 0.1 mm, preferably less than 0.5 mm. A ribbon configuration can also serve as a drug-eluting barrier that separates tissue structures of similar or different composition.

A variety of polymers may be suitable to form the thread or fiber, bulb(s), and ribbon(s) of the present invention. Preferable polymers are largely insoluble in physiological fluids. Suitable polymers may include naturally occurring or synthetic polymers. Certain exemplary polymers include, but are not limited to, Dexon, Vicryl, Polysorb, poly(lactide-coglycolide) (PLGA), polyglycolic acid (PGA), polylactic acid (PLA), polycaprolactone (PCL), polydioxanone (PDO), polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, polyvinyl acetates, plasticized ethylene vinylacetate copolymer, polyvinyl alcohol, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly(1,4-isopropylidene diphenylene carbonate), vinylidene chloride, acrylonitrile copolymer, vinyl-chloride-diethyl fumerate copolymer, silicone rubbers, medical grade polydimethylsiloxanes, ethylene-propylene rubber, silicone-carbonate copolymers, vinylidene chloride-vinyl chloride copolymer, vinyl chloride-acrylonitrile copolymer, vinylidene chloride-acrylonitrile copolymer, etc.

The instant invention may employ polymers such as PGA, PLGA, etc., which are FDA approved. Some embodiments employ PLGA in particular. It is known that PGA, PLA and PLGA can be prepared as monofilament fibers by wet-spinning (Nelson et al., 2003 and references therein).

The therapeutic agent may range from a nucleic acid (such as a vector, an RNAi construct, or an antisense oligonucleotide) or protein to a small organic molecule. In certain embodiments, the agent is an anti-cancer (such as camptothecin or related derivatives), anti-fungal, anti-bacterial, anti-mycotic, or anti-viral therapeutic. In certain embodiments, the agent is a receptor antagonist. In certain embodiments, the therapeutic agent is a protease inhibitor. In certain embodiments, the therapeutic agent is a nerve growth factor. Furthermore, a polymer of the present invention may contain one kind of therapeutic agent or may contain more than one kind of therapeutic agent. For instance, two or more different cancer drugs, or a cancer drug and an immunosuppressant, or an antibiotic and an anti-inflammatory agent may be included in the composition.

In certain embodiments, the drug-polymer-thread or fiber may be used as a suture to treat wounds (i.e., to promote wound healing). For example, when fibers or threads of the invention are combined or braided with non-absorbable suture materials, the suture may provide both permanent suture strength and local drug delivery. Such compositions may also include as the drug or agent, for example, PDGF-B or an expression vector for producing PDGF-B in a target cell, stimulators of cell proliferation or differentiation, stem cells or progenitor cells, and/or other compounds known to be effective in promoting tissue repair, healing, inhibiting infection, etc., such as growth factors, including protein growth factors. In an illustrative example, a suture comprising a non-absorbable suture fiber and a biodegradable fiber containing a growth factor may be employed in the repair of torn tendons or ligaments.

In some embodiments, the present biodegradable implant system containing corticosteroid, anti-inflammatory drug, angiogenesis-inhibiting agent, or anti-metabolite drug may be used to inhibit pathologic fibrosis, scarring, and neovascularization. For example, the system can be used in the prevention of keloid formation after skin wound healing by using a corticosteroid-eluting thread or fiber to reduce fibrosis.

According to an aspect of the invention, biodegradable polymer with a ribbon configuration containing corticosteroid or 5-fluorouracil, for example, may function as a drug-eluting barrier and be used to separate tissue structures and prevent adhesions of tissues. A biodegradable ribbon implant system containing corticosteroid or 5-fluorouracil may also be used to improve glaucoma surgery outcomes by reducing postoperative fibrosis and scarring. The use of a biodegradable ribbon implanted at the time of glaucoma surgery to provide sustained release of 5-fluorouracil may provide improved performance and convenience over the multiple postoperative sub-conjunctival injections presently used.

In a further embodiment, a biodegradable thread or fiber containing an angiogenesis-inhibiting agent, a corticosteroid, or other drugs, may be used to treat age-related macular degeneration with subretinal neovascularization. The drug eluting thread or fiber may be placed in the sclera over the neovascular net or placed sub-retinal in the area of the neovascular net.

In other embodiments, compositions of the invention may be used in the treatment of cancer. The thread or fiber may be implanted into the tissue surrounding the tumor or into the tumor tissue and tied in place to deliver local drug therapy. For example, sutures and related compositions containing an anti-cancer agent may be used to close incisions produced from invasive surgical procedures associated with cancer treatment, such as tumor removal, in particular from removal of tumors on or near the skin of the patient. Such tumors may result from various forms of skin cancer, such as basal cell carcinoma or melanoma. Such compositions may include a chemotherapeutic agent, an angiogenesis-inhibiting agent, a cell proliferation inhibitor, a radiosensitizer, and/or any other agent useful in the treatment of cancer.

For example, compounds that may be formulated in a subject composition for the treatment of cancer include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prednisolone); growth factor signal transduction kinase inhibitors; mitochondrial dysfunction inducers and caspase activators; chromatin disruptors.

The drug or agent delivered by the present system may also include but not be limited to steroids, such as corticosteroids, retinoids, NSAIDs, vitamin D3 and vitamin D3 analogs, antibiotics, and antiviral agents. Other suitable agents include enzymes, peptides and other large molecules.

Suitable steroids include but are not limited to androgenic and estrogenic steroid hormones, androgen receptor antagonists and 5-α-reductase inhibitors, and corticosteroids. Specific examples include but are not limited to alclometasone, clobetasol, fluocinolone, fluocortolone, diflucortolone, fluticasone, halcinonide, mometasone, prednisone, prednisolone, methylprednisolone, triamcinolone, betamethasone, and dexamethasone, and various esters and acetonides thereof.

Suitable retinoids include but are not limited to retinol, retinal, isotretinoin, acitretin, adapalene, tazarotene, and bexarotene.

Suitable NSAIDs include but are not limited to naproxen, suprofen, ketoprofen, ibuprofen, flurbiprofen, diclofenac, indomethacin, celecoxib, and rofecoxib.

Suitable vitamin D3 analogues include but are not limited to doxercalciferol, seocalcitol, calcipotriene, tacalcitol, calcitriol, ergocalciferol, and calcifediol.

Suitable antiviral agents include but are not limited to trifluridine, cidofovir, acyclovir, penciclovir, famciclovir, valcyclovir, gancyclovir, and docosanol.

Suitable human carbonic anhydrase inhibitors include but are not limited to methazoliamide, acetazolamide, and dorzolamide.

Suitable antiproliferative agents include but are not limited to 5-FU, taxol, daunorubicin, and mitomycin.

Suitable antibiotic (antimicrobial) agents include but are not limited to bacitracin, chlorhexidine, chlorhexidine digluconate, ciprofloxacin, clindamycin, erythromycin, gentamicin, lomefloxacin, metronidazole, minocycline, moxifloxacin, mupirocin, neomycin, ofloxacin, polymyxin B, rifampicin, ruflozacin, tetracycline, tobramycin, triclosan, and vancomycin. The antiviral and antibacterial prodrugs of the invention may be used to treat appropriately responsive systemic infections.

The agent may be dissolved, dispersed or suspended in the polymer of the thread, whereupon it may leach out of the thread and into surrounding fluid. In certain embodiments, the agent may rapidly escape from a thread after placement in a physiological system. Such rapid delivery of drug may delivery a large burst of drug to a targeted tissue and provide a spike in drug level within the tissue.

In certain embodiments, the polymeric components of the thread are biocompatible and may dissolve when in contact with physiological fluid. The rate at which such components dissolve may impact the rate of release of the agent. In certain embodiments, as the thread component(s) erode or dissolve, the rate of release of the agent may increase. For example, in certain embodiments, less than about 10% of the polymeric component(s) may erode or dissolve over a period of about 6 hours. This may increase the rate of release of the agent by less than about 10% over that time. In certain embodiments, the polymeric component(s) may erode or dissolve more slowly (e.g. less than about 10% over a period of about 24 hours, or even over a period of multiple days, weeks, or even months). In certain embodiments, such erosion or dissolution may occur more rapidly (e.g. greater than about 10% over a period of about 6 hours, in certain embodiments even greater than 25% over a period of about 6 hours).

In certain embodiments, the solubility of the agent in the polymer impacts the rate of release of the agent from the thread. In certain embodiments, the agent is soluble, moderately soluble, or even slightly soluble or very slightly soluble in the polymer. The agent's release rate from the thread where an agent is soluble in the polymer may exceed the rate of release where the agent is only slightly or very slightly soluble in the polymer.

In certain embodiments, the release rate of the agent from the thread may be controlled by the ratio of the agent to the polymeric component of the thread (also referred to as the "drug loading"). By changing the drug loading, different release rate profiles can be obtained. Increasing the drug loading may increase the release rate. For a slower release profile, drug loading may be less than 10%, and preferably less than 5%. For a faster release profile, drug loading may be more than 10%, and preferably more than 20%, or even greater than 50%. The drug loading can be tuned and/or optimized for specific applications based on the fabrication method of the fiber and/or through the addition of additives and/or carrier molecules, such as cyclodextrins.

In certain embodiments, the agent may have low solubility in the physiological fluid immediately surrounding the implanted/inserted thread. In such embodiments, the rate of release of the agent from the thread may be controlled by the solubility of the agent in such surrounding fluid (i.e., the lower the solubility of the agent in the immediately surrounding fluid the lower its rate of release from the thread or fiber).

In certain embodiments, the thread may contain additives that can be used to tune the drug delivery profile of the system. Examples include water soluble additives such as sugars, salts, or poly(ethylene oxide) or poly(ethylene glycol) and derivatives and copolymers thereof.

The drug or agent may be associated with a delivery system, e.g., a nucleic acid may be contained in a virus, or an agent may be carried within liposomes or microspheres, and the delivery system is dispersed through the polymeric components of the thread.

In order to optimize the mechanical and drug release profiles of the thread, polymers mixed with inclusion hosts as additives or bearing or including inclusions hosts in their backbone or side chains may also be employed. Cyclodextrins (CDs) are one example of such an inclusion host and may be employed with any of the polymers of the instant invention. Cyclodextrins have a ring structure which has a basket-like shape. This shape allows cyclodextrins to include many kinds of molecules into their internal cavity. See, for example, Szejtli, *Cyclodextrins and Their Inclusion Complexes*; Akademiai Klado, Budapest, 1982; and Bender et al., *Cyclodextrin Chemistry*, Springer-Verlag, Berlin, 1978. Cyclodextrins are able to form inclusion complexes with an array of organic molecules including, for example, drugs, pesticides, herbicides, and agents of war. See, Tenjarla et al., *J. Pharm. Sci.*, 87: 425-429 (1998); Zughul et al., *Pharm. Dev. Technol.*, 3: 43-53 (1998); and Albers et al., *Crit. Rev. Ther. Drug Carrier Syst.*, 12: 311-337 (1995). CDs such as PCD (Nagaraju et al., 1999; Chao et al., 2002), HPβCD (Chao et al., 2004) and SBEβCD (Babu et al., 2004) have successfully been used to form individual complexes with ciprofloxacin. Cyclodextrin inclusion complexes have also been prepared with prednisolone. HPβCD (Loftsson et al., 1994) and SBEPCD (Okimoto et al., 1998) have been used successfully to form inclusion complexes with prednisolone.

Linear cyclodextrin-based polymers (CDPs) have previously been shown to have low toxicity both in vitro (in many different cell lines) and in vivo. See Gonzalez et al. *Bioconjugate Chem* 10:1068-1074 (1999) and Hwang et al. Bioconjugate Chem 12(2):280-290 (2001). The presently disclosed thread or fiber system includes biocompatible materials based on polymers that may bear or include cyclodextrin moieties. One or more linear CDPs of the same or different identities may be used as polymeric components in the thread.

The therapeutically active drug or agent may form an inclusion complex with the cyclodextrin moiety. Alternatively, a functional group or side group on the drug may form an inclusion complex with the cyclodextrin moiety. The specific interaction between the cyclodextrin and the drug may be determined by judicious selection of the cyclodextrin moiety. The interaction between the cyclodextrin and the drug may enhance the solubility properties of the drug. The drug may be more or less soluble in aqueous media on complexation with a cyclodextrin. The interaction between the cyclodextrin and the drug may be used to tune the controlled release of the drug from the thread or fiber. It has recently been shown that CD/drug complexes can be combined with polymers to provide for controlled release of the drug. For example see Loftsson, et al. *J. Drug Del. Sci. Tech.* 14: 35-43 (2004) and references therein or Yue, et al. *Biomaterials* 25:3743-3750 (2004). In a preferred embodiment, the combination of CD/drug complexes when used with biodegradable polymers will provide the necessary mechanical and drug release properties to enable the use of thread for the controlled release of drugs.

In addition to cyclodextrins of various types and sizes, derivatives of these cyclodextrins such as methylated, alkylated, acylated, and benzylated cyclodextrins may be chosen to tune the drug delivery properties of the current system. Furthermore, unsaturated as well as homo-, seco-, and nor-derivatives of cyclodextrins may also be used. The present system also accommodates various substitution on the cyclodextrins or their derivatives. Such substitutions may improve the properties of the system, such as drug release profile, binding properties, solubility, and or bioavailability. While not intended to be limiting, some examples of β-cyclodextrins are shown below:

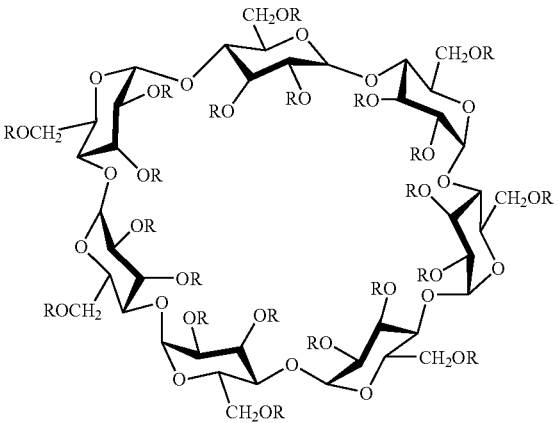

Dimethyl-β-cyclodextrin (DMPCD) —CH$_3$ or —H
Trimethyl-β-cyclodextrin (TMβCD) —CH$_3$
Randomly methylated-β-cyclodextrin (RMβCD) —CH$_3$ or —H
Hydroxyethyl-β-cyclodextrin (HEβCD) —CH$_2$CH$_2$OH or —H
2-Hydroxypropyl-β-cyclodextrin (HPβCD) —CH$_2$CHOHCH$_3$ or —H
3-Hydroxypropyl-β-cyclodextrin (3HPβCD) —CH$_2$CH$_2$CH$_2$OH or —H
2,3-Dihydroxypropyl-β-cyclodextrin (DHPβCD) —CH$_2$CHOHCH$_2$OH or —H
2-Hydroxyisobutyl-β-cyclodextrin (HIBβCD) —CH$_2$C(CH$_3$)$_2$OH or —H Sulfobutylether-β-cyclodextrin (SBEβCD) —(CH$_2$)$_4$SO$_3$Na or —H Glucosyl-β-cyclodextrin (G$_1$βD)-glucosyl or —H Maltosyl-β-cyclodextrin (G$_2$βCD)-maltosyl or —H In certain embodiments of the present invention, a polymer bears both inclusion hosts and inclusion guests, and thus crosslinks with itself by forming inclusion complexes between hosts and guests on the same polymer chain and/or between hosts and guests on adjacent polymer chains. Conditions under which the crosslinking is performed will influence the balance between these two types of inclusion complexes. For example, performing the complexation at high dilution will favor the formation of intramolecular complexes, while performing the complexation at high concentrations will favor the formation of intermolecular complexes, including, in some cases, catenane- and rotaxane-type structures. In certain such embodiments, a high degree of intermolecular interaction increases the rigidity, melting point, and strength of the material.

For purposes of the present application, polymers 'incorporate' inclusion hosts, such as cyclodextrin moieties, by having inclusion hosts within the polymer chain, e.g., removing inclusion hosts from the polymer would require severing the polymer chain. Examples of such polymers are the linear cyclodextrin-based polymers referred to above. Polymers that 'bear' cyclodextrin moieties have a polymer chain to which inclusion hosts are attached, e.g., inclusion hosts are appended to a distinct polymer chain. Polyethylenimine-CD polymers are examples of this type of polymer. Polymers that 'include' inclusion hosts are those polymers that 'bear' or 'incorporate', or both bear and incorporate, inclusion hosts, or otherwise have covalently bound inclusion hosts as part of the polymer chain. Any polymer that includes inclusion hosts can be employed in the present application. In certain embodiments, a polymer that incorporates inclusion hosts is a linear (i.e., non-branched) polymer. In certain embodiments, inclusion hosts, e.g., incorporated into or borne on the polymer, are regularly spaced throughout or along the polymer.

The physical and drug release properties of the resultant fiber or thread can be varied by selecting moieties or drugs that form inclusion complexes of varying strength; the stronger the complex, the more durable and stable the resulting system and the slower the release of therapeutic agent. Additionally, the physical and drug release properties of the instant system may be tuned by covalently attaching the drug or agent to the polymeric component(s) of the thread or fiber system. Such attachment may utilize linking moieties. Such linking moieties may be cleaved under biological and/or physiological conditions, thereby releasing the drug or agent. Alternatively, such linking moieties can be used to connect two or more drugs or agents of the same or different identities, while remaining non-covalently associated with the polymer. The linking moieties can also be used to crosslink polymers within the fiber or polymers within different fibers. As such, linking moieties can be used to link two or more fibers in a thread. Linking moieties bearing two or more such drug moieties may increase the strength and rigidity of the material by increasing the degree of crosslinking as well as increasing the proportion of linking moieties to polymer mass. The drug release profile of the system may also be varied in this manner as multiple therapeutic agents may be tethered or linked together in one molecule. Following release of such a molecule from the polymeric component(s) of the thread, the tether or linking moiety can be cleaved under physiological conditions releasing multiple therapeutic agents. Additionally, varying the number of binding therapeutic agents will alter the binding capacity, and hence the drug release profile.

Physical properties of the thread can also be varied by altering the flexibility of the linking moieties themselves, or by altering the flexibility of linkers within the polymer itself.

Furthermore, the in vivo properties of the polymer system may be varied by using bonds in the polymer that are labile under physiological conditions. For example, the polymer strands, the crosslinking moieties, or both, may comprise bonds, such as ester and peptide bonds that are labile under physiological conditions. After placement in a physiological environment, these bonds will gradually begin to cleave, resulting in a gradual degradation and loss of structural integrity. A wide spectrum of properties can be achieved by varying the frequency of such bonds in a polymer strand, by combining labile and resistant crosslinking moieties in varying proportions, or by selecting different labile bonds with differing strengths. For example a peptide bond is generally more resistant to cleavage than an ester bond, which is in turn less labile than a thioester bond.

Inclusion hosts, such as cyclodextrins, can be used with the polymeric components of the thread through covalent bonds. These hosts can be directly on the polymer backbone or on side chains. Alternatively, the hosts, such as one or more types of cyclodextrins, can be admixed into the polymer blend. A combination of covalently bound hosts and non-covalently bound hosts can also be used, wherein the hosts may be the same or different throughout the thread or fiber system. Furthermore, the polymer system may be made up of predominantly or entirely of cyclodextrins, of which there may be one or more types. Therapeutic agents, viruses, adjuvants, and the like, which can be formulated with the polymer by forming inclusion complexes, can also be formulated by simple admixture or encapsulation, without forming inclusion complexes, as is well known in the art for ordinary biocompatible polymers.

Compounds increasing the therapeutic utility of the material, such as signaling peptides, other moieties facilitating cell migration, or adjuvants, may be incorporated into the polymer by conjugating an inclusion complex guest to the entity of interest and including the conjugate in the polymer. The conjugate may be included before, during or after the formation of the polymer or during or after the formation of the thread from the polymer. Therapeutic compounds may also be included in this fashion, preferably where the attachment between the drug and the inclusion guest/host is labile under physiological conditions, such as an ester bond. See U.S. patent application Publication Nos. 20030008818 and 20030017972.

Additionally, those of skill in the art will recognize that this concept can naturally be extended to polymers bearing or incorporating inclusion hosts other than cyclodextrins, in conjunction with linking moieties that bear inclusion guests that form inclusion complexes with those inclusion hosts, or, alternatively, polymers that bear inclusion guests in conjunction with linking moieties that bear or include inclusion hosts that form inclusion complexes with those inclusion guests. Examples of inclusion hosts other than cyclodextrins and related cycloamyloses include perhydrotriphenylene (which forms inclusion complexes with polyethylene), urea/thiourea (which form inclusion complexes with fatty acids and related molecules as described in U.S. Pat. Nos. 4,776,984, 5,106,542, and 4,170,601), cyclophanes (such as those described in U.S. Pat. No. 4,116,955), and those described in U.S. Pat. Nos. 4,841,081, 4,367,072, and 4,898,654, all of which are hereby incorporated by reference in their entireties.

The foregoing factors are illustrative only. The skilled artisan will readily appreciate that any other property of the inventive system may be the limiting factor in the agent's release rate from the system.

The fiber or thread disclosed herein, in addition to being potentially biodegradable, may also incorporate a biodegradable coating. Coatings containing caprolactone a for synthetic absorbable sutures are well known, see for example U.S. Pat. Nos. 4,624,256; 4,190,720; 4,582,052; 4,605,730; 4,700,704; 4,705,820; 4,788,979; 4,791,929; 4,994,074; 5,047,048; 5,100,433; 5,133,739; 5,352,515. Coatings containing esters of fatty acids are also known; see for example U.S. Pat. Nos. 5,032,638, 4,711,241, 4,705,820, and 4,027,676. Advantages of using coated fiber or thread include reduction in the incidence of tissue trauma (tissue drag) as compared to use of uncoated braided multifilament thread. Another important feature of a coating is its ability to enhance the thread's handling characteristics, such as surgeon's throw, lubricity, knot run down and/or knot security. The coating of the fiber or thread may also incorporate one or more drugs or therapeutic agents to provide an initial burst or surge of therapeutically effective drug to the targeted tissue, followed by sustained release of the drug or agent from the degradation of the remainder of the polymer system. Such a drug may be dissolved in the coating in similar methods as described herein for drugs dissolved in the thread. Similarly, the coating may be composed of materials that may be the same or different from that of the thread or fiber system. Numerous biodegradable surface coated sutures have been FDA approved and are currently in use. For example, U.S. Pat. No. 5,716,376, all of which may be adapted to the present invention and the disclosure of which is incorporated herein by reference, describes a copolymer bioabsorbable coating.

2. Definitions

For convenience, before further description of the present invention, certain terms employed in the specification, examples, and appended claims are collected here. These definitions should be read in light of the remainder of the disclosure and understood as by a person of skill in the art.

The term "active" as used herein means biologically, therapeutically or pharmacologically active.

An 'adjuvant', as the term is used herein, is a compound that has little or no therapeutic value on its own, but increases the effectiveness of a therapeutic agent. Exemplary adjuvants include radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.

The term "agent" as used herein is synonymous with "at least one agent," "compound," or "at least one compound," and means at least one drug or codrug, or a prodrug thereof. In certain embodiments, the agent may be at least one low-solubility codrug, or a prodrug thereof. In certain embodiments the codrug, or prodrug thereof, is designed to have low solubility in either the core, the biological fluid or both. In certain embodiments, the agent may be a protein, peptide, or a pegylated agent. In still other embodiments, the term "agent" refers to a plurality of drugs, proteins, peptides, etc. In certain embodiments the agent may be in granular form. In certain embodiments, the agent may be combined with a pharmaceutically acceptable carrier. In certain embodiments, the agent is in liquid form.

The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction, in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 µL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The term "biodegradable" is synonymous with "bioerodible" and is art-recognized. It includes polymers, compositions and formulations, such as those described herein, that degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, biodegradation may occur by enzymatic mediation, degradation in the presence of water and/or other chemical species in the body, or both.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any biodegradable polymer is usually slower.

In certain embodiments wherein the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of material(s) incorporated therein.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the polymer degrades in a period of between about one hour and several weeks, depending on the desired application.

The term "delivery agent" is an art-recognized term, and includes molecules that facilitate the intracellular delivery of a therapeutic agent or other material. Examples of delivery agents include: sterols (e.g., cholesterol) and lipids (e.g., a cationic lipid, virosome or liposome).

The term "drug delivery device" is an art-recognized term and refers to any medical device suitable for the application of a drug or therapeutic agent to a targeted organ or anatomic region. The term includes, without limitation, those formulations of the compositions of the present invention that release the therapeutic agent into the surrounding tissues of an anatomic area.

When used with respect to a therapeutic agent or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, lymph or the like, the polymer matrices (formulated as provided herein and otherwise as known to one of skill in the art) may undergo gradual degradation (e.g., through hydrolysis) with concomitant release of any material incorporated therein, e.g., an therapeutic and/or biologically active agent, for a sustained or extended period (as compared to the release from a bolus). This release may result in prolonged delivery of therapeutically effective amounts of any incorporated therapeutic agent. Sustained release will vary in certain embodiments as described in greater detail below.

An "effective amount" or "therapeutically effective amount" of an agent, with respect to methods of treatment, refers to an amount of the agent in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose. A therapeutically effective amount, as recognized by those of skill in the art, will be determined on a case by case basis. Factors to be considered include, but are not limited to, the disorder to be treated and the physical characteristics of the one suffering from the disorder.

As used herein, the term "$EC_{50}$" means the concentration of a drug that produces 50% of its maximum response or effect.

As used herein, the term "$ED_{50}$" means the dose of a drug that produces 50% of its maximum response or effect.

The terms "encapsulated" is art-recognized when used in reference to a therapeutic agent, or other material and a polymeric composition, such as a composition of the present invention. In certain embodiments, these terms include incorporating, formulating, or otherwise including such agent into a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to-the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved, in the polymer. Any form of encapsulation or incorporation is contemplated by the present invention, in so much as the release, preferably sustained release, of any encapsulated therapeutic agent or other material determines whether the form of encapsulation is sufficiently acceptable for any particular use.

The term "fiber" as used herein, refers to a slender, elongated, wire-like object or structure. "Fiber" and "filament" are used interchangeably herein. A fiber of the present invention refers to a biodegradable drug-eluting polymer with a slender, elongated shape. In certain embodiments, "fiber" as used herein, also includes one or more sections which possess a ribbon configuration comprising a flexible, flat and/or thin profile or shape. In some embodiments, "fiber" as used herein, also includes one or tube configurations; that is, elongated structures with a hollow core at their centers, for example, tube-like structures. As such, a fiber of the present invention may also refer to a biodegradable drug-eluting polymer tube, i.e., a fiber fashioned to include a hollow portion in its center, such as a longitudinally extending through lumen. In certain embodiments, a fiber comprises portions that have different physical characteristics and or configurations, e.g., ribbon portions, hollow portions, bulb portions, or different chemical characteristics, e.g., polymers or polymer blends, additives, or the like.

The term "$IC_{50}$" means the dose of a drug that inhibits a biological activity by 50%.

The term "$LD_{50}$" means the dose of a drug that is lethal in 50% of test subjects.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filter, diluent, excipient, solvent or encapsulating material suitable for formulating a medical or cosmetic composition. Each carrier must be "acceptable" in the sense of being compatible with other ingredients of the formulation and not injurious to the patient.

Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, analgesic agents, therapeutic agents, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.* 66: 1-19 (1977).

"Physiological conditions" describe the conditions inside an organism, i.e., in vivo. Physiological conditions include the acidic and basic environments of body cavities and organs, enzymatic cleavage, metabolism, and other biological processes, and preferably refer to physiological conditions in a vertebrate, such as a mammal.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The phrase "protecting group" or "protective group" as used herein means a temporary substituent that protects a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

As used herein, the term "RNAi construct" is a generic term including small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

The phrases "systemic administration," "administered systemically," "peripheral administration" and "administered peripherally" are art-recognized, and include the administration of a subject composition, therapeutic or other material at a site remote from the disease being treated. Administration of an agent directly into, onto, or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The term "therapeutic index" refers to the therapeutic index of a drug defined as $LD_{50}ED_{50}$.

The term "thread" as used herein includes one or more fibers or filaments, at least one of which may be a biodegradable drug-containing fiber of the present invention. When a thread comprises more than one fiber, the fibers may be twisted, interwoven, spun, tufted, or otherwise braided together to form the thread. Thus, threads of the present invention include monofilaments, braided polyfilaments, and other associations of multiple fibers. The systems and methods described herein are amenable to the use of the present threads and/or fibers, unless specifically stated to the contrary. For example, in some embodiments, threads may also possess one or more ribbon configurations and/or tube configurations.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

3. Exemplary Applications of Methods and Compositions

The person skilled in the art will recognize that additional embodiments according to the invention are contemplated as being within the scope of the foregoing generic disclosure, and no disclaimer is in any way intended by the foregoing, non-limiting examples.

One embodiment of the present systems relates to a biodegradable polymeric thread or fiber that contains single or multiple therapeutic agents or drugs within the body of the thread or fiber to provide a biodegradable drug-eluting suture. Such a system may be employed in the treatment of ocular diseases and disorders. The suture may provide sustained release of one or more therapeutic agents or drugs over the lifetime of the suture as it degrades. Such a system may provide high and/or stable intraocular levels of therapeutic agent or drug in contrast to methods of treatment employing topical drops. In some embodiments, drug-eluting sutures may decrease and/or eliminate the need to employ eye drop treatments after surgeries. Such instant methods may reduce and/or eliminate patient compliance issues.

The drug-eluting suture may be attached to a surgical needle. In certain embodiments, the needle can be used to penetrate the conjunctiva and to deliver the attached drug-eluting suture into the sub-conjunctival space. FIGS. 3a and 3b present schematic illustrations of the anatomy of the eye, highlighting the conjuctiva. Once the biodegradable suture is implanted under the conjunctiva, the suture may be cut close to the surface of the conjunctiva, so only a small suture tail remains. In certain embodiments, the suture is placed in the conjunctival fornix (junction between the posterior eyelid and the eyeball) where it is covered by the eyelid. FIG. 4 presents a photograph illustrating the lower lid conjuctival fornix. As the suture degrades, one or more therapeutic agents or drugs may be released into the sub-conjunctival space and into the fornix to mix with the tear film and subsequently into the eye. By placing the suture under the conjunctiva, foreign body sensation may be reduced or eliminated, and the suture will not migrate or dislodge.

The drug-eluting sutures may be useful in many instances for methods of treatment, such as ocular treatment. Sutures and/or one or more variants of the instant invention may have wide applicability and be useful for virtually all ophthalmic surgery. In one embodiment, the sutures may be employed with post-operative antibiotics and corticosteroids. The conjunctiva may be anesthetized for a primary surgery. The use of sutures of the instant invention may employ instruments available in standard surgical facilities and operating rooms. The methods of treatment comprising the instant sutures may lessen or eliminate the need for treatment with eye drops following surgical procedures. In instances where the current method substitutes for treatment with eye drops, the convenience to the patient and therefore patient compliance may increase, particularly in cases where the patient is resistant to applying eye drops following surgery.

For example, an illustrative clinical application of the present suture system is treatment of a postoperative cataract patient. Drops are routinely used after cataract surgery: corticosteroids are used postoperatively for 3 to 4 weeks and antibiotics for one to two weeks. A biodegradable suture of the present invention comprising the present fibers or threads containing corticosteroid and antibiotic may be implanted in the sub-conjunctival space at the time of cataract surgery to provide sustained postoperative drug release. Differences in duration and rate of drug delivery may be modulated by fiber size, shape and polymeric/chemical make up. Such a sustained drug release has a distinct advantage over the usual postoperative drops, because the implant drug delivery does not depend on patient compliance and systemic doses are avoided.

In another illustrative example, drug-containing sutures of the present system, such as corticosteroid sutures, may be imbedded in lesions such as eyelid chalazion to reduce inflammation, or hemangiomas to reduce vascular mass.

The instant sutures may also provide methods of antibiotic treatment to patients suffering from corneal ulcers. In such embodiments, the instant polymeric suture may provide sustained levels of antibiotic, which may be important as the cornea is avascular. Such instant methods may diminish and/or replace repeated, often hourly, application of eye drops, especially in instances where application of drops is painful to the patient.

The instant sutures may also provide methods of treatment to patients requiring corticosteroid treatment of uveitis and scleritis. In such embodiments, the instant polymeric suture may facilitate long-term treatment and/or treatment when patients are asymptomatic. The instant methods and systems may be used to taper the dose of the therapeutic agent or drug employed The instant sutures may also provide methods of antibiotic treatment to patients requiring treatment for glaucoma. In such embodiments, the instant polymeric suture may facilitate long-term treatment and/or treatment when patients are asymptomatic. Often sufferers of glaucoma are elderly and may have difficulty administering treatment by eye drops; the instant methods will facilitate treatment by reducing and/or obviating the need for drops. The instant system can deliver controlled amounts of therapeutic agent or drug to facilitate compliance. The instant methods and systems may be used to taper the dose of the therapeutic agent or drug employed.

The instant sutures may also provide methods of treatment to suffering from vernal conjunctivitis. In such embodiments, the instant polymeric suture may facilitate long-term treatment and/or treatment when patients are asymptomatic.

The drug-eluting polymeric threads or fibers of the present invention may contain any of the therapeutic agents or drugs described herein. In certain embodiments, the polymeric sutures for ocular treatment may contain antibiotics, such as ciprofloxacin. In certain embodiments, the polymeric sutures for ocular treatment may contain steroids, such as the corticosteroid prednisolone. In some embodiments the polymeric sutures for ocular treatment may contain more than one therapeutic agents or drugs in combination. Such combinations may employ agents of the same or of different types. For example, the antibiotic ciprofloxacin and the corticosteroid prednisolone may be used in combination.

Another embodiment of the present systems relates to a biodegradable polymeric thread or fiber that contains single or multiple therapeutic agents or drugs for the treatment of diseases or inflammations of the mouth, in particular those of the teeth and gums, such as gingivitis or periodontitis. In one embodiment, the fiber or thread contains one or more drugs or agents, such as an antibiotic, and is implanted into the periodontal tissue to provide local drug delivery as the fiber or thread degrades. The fiber or thread may be placed in the subgingival tissues. In some embodiments, the fiber or thread provides sustained local delivery of the agent resulting in sustained elevated agent concentrations in the crevicular fluid; in other embodiments, the fiber or thread provides an initial burst of the agent. In certain embodiments, the antibiotic agent is chlorhexidine, metronidazole, minocycline, triclosan, or tetracycline.

Treatment of periodontitis with the present system may be more effective than traditional scaling, root planing, and antibiotic mouthrinse methods. Additionally, the fibers or threads of the invention can be used in combination (i.e. in adjunctive therapy) with other suitable periodontal treatment methods, such as scaling, root planing, and antibiotic mouthrinse methods. The present system may also provide advantages and/or improved efficacy over other agent-releasing implants, such as fibers, chips and/or gels. For example, the present fibers or threads may provide sustained local delivery of a therapeutic agent to the periodontal tissues, reducing the frequency of treatment when compared with other implantation or treatment methods. The current system may also prove effective for treatment of periodontitis where other treatments, such as scaling, root planing, antibiotic implants, or combinations thereof, have proven ineffective; for example, the fibers or threads of the invention may prove effective for treating periodontitis in a patient that has previously not responded to other treatments. Periodontal treatment by the present invention may enhance surface demineralization, delay pellicle and plaque formation, promote anti-collagenase activity, reduce periodontal pocket depth, and reduce bleeding on probing.

In another embodiment, the present invention relates to the use of biodegradable therapeutic agent-containing fibers or threads as biodegradable nerve guide tubes. Fibers or threads of the invention may contain a hollow core, e.g., a longitudinally extending lumen, to provide a tube-like structure. Such a tube may be used as a guide to induce nerve growth between ends of a severed nerve and/or to connect transected axons. Thus, nerve guide tubes or nerve guides of the present invention can be used to repair peripheral nerve damage and/or to reduce or eliminate neuropathic pain that may result from such damage. Nerve guides of the present invention may be inert and biocompatible, thin, flexible, of suitable mechanical properties, and beneficial to healing and/or regeneration. In certain embodiments, the nerve guides are biodegradable or bioresorbable. In some embodiments, the nerve guides are able to inhibit pathological processes. In some embodiments, the nerve guides are translucent.

Fibers of the present invention possessing a tube-like structure or configuration may be anywhere from a few millimeters long to several centimeters long or longer. The internal diameter of the tubes may be approximately 5 mm, 2 mm, 1 mm, 0.5 mm, 0.1 mm or less, preferably less than about 1 mm. The wall of the tube may be approximately 2 mm, 1 mm, 0.5 mm, 0.1 mm, 0.01 mm or less, preferably less than about 0.1 mm.

In certain embodiments, the wall of the hollow fiber, e.g., the nerve guide, is loaded with one or more therapeutic agents, such as neurotrophic factors, e.g., nerve growth factor (NGF), brain-derived neurotrophic factor (BDNF), and other factors present in regenerating peripheral nerves. In some embodiments, one or more optional additives and/or carrier molecules, such as a cyclodextrin, may be loaded into the fiber. In some embodiments, the wall of the hollow fiber is loaded with one or more nerve growth inducing agents. Such agents may be a small molecules, such as sabeluzole or inosine, or a larger biological molecule, such as human nerve growth factor. Examples of nerve growth factors suitable in the present invention include proteins and nucleotides. The present system also contemplates low temperature methods of nerve guide tube fiber production, such as wet-extrusion and dip-coating, which may be compatible with the incorporation of biological nerve growth factors, such as proteins and nucleotides. The nerve guide tubes may also include biodegradable drug delivery agents, such as microspheres or nanofibers, which may be included in the walls of the fiber or inside the hollow core of the fiber. The nerve guide tubes may induce nerve growth by both the physical presence of a tube and by the controlled release of nerve growth factors. Once the nerve has regenerated, the tube itself may biodegrade, eliminating the need to remove the tube. Alternatively, the tube may be easily removed prior to its biodegradation; thus implantation of the guide tube may be reversible.

In some embodiments, the hollow core of the nerve guides may be filled with a drug-containing and/or releasing medium. For example, the tubes may contain a gel or hydrogel, such as collagen containing a therapeutic agent, such as a growth factor. In certain embodiments, the nerve guides are filled with an isotropic collagen gel or a magnetically aligned hydrated gel of type I collagen. The nerve guides may also contain microspheres or beads which contain and release one or more therapeutic agents, such as NGF. In certain embodiments, the nerve guides may contain NGF-secreting cells, such as Schwann cells. Additionally, the medium contained within the nerve guide may also release one or more additives and/or carrier molecules, such as cyclodextrins, which may facilitate the loading of the agent and/or its delivery from the nerve guide.

Fibers of the present invention that are used as nerve guides may possess any of the features of other fibers described herein. For example, nerve guides may comprise a variety of biodegradable polymers, such as polyphosphoester, polylactic acid (PLA), polycaprolactone (PCL), polyglycolic acid (PGA), polydioxanone (PDO), or co-polymers thereof, such as PLA-PCL, PGA-PCL, PCL-PDO, etc. Other examples of polymers suitable for use in fibers of the present invention, particularly for nerve guides, include poly(1,3-trimethylene carbonate-caprolactone) and poly(bis(hydroxyethyl)terephthalate-ethyl ortho-phosphorylate/terephthaloyl chloride). The instant nerve guides may also include other materials such as metals, silicone, rubbers, and both biodegradable and non-biodegradable synthetic polymers.

Examples of nerve guide tubes contemplated by the present invention include those described in U.S. Pat. No. 3,833,002; Rosner, et al. *Ann. Biomed. Eng.* 2003, 31, 1383-1401 and Verreck et al. *Biomaterials,* 2005, 26, 1307-1315; the entire contents of which are hereby incorporated by reference.

In another embodiment, fibers or threads of the present invention having a tube configuration may be employed as a stent, i.e. a tube like device to create patency, to hold anatomic tubes open. The instant stents may have certain the features from other fibers described herein. For example, the stents may elute one or more drugs or therapeutic agents and/or contain one or more additives or carrier molecules, such as cyclodextrins. The stents may have one or more biodegradable portions. Additionally, the present stents may include one or more non-biodegradable portions, for example, made from traditional stent materials, such as stainless steel or other metals or plastics. The present stents may be installed by any suitable means, for example, by those used for traditional stents. In certain embodiments, the present stents may also be readily removed from the patient, i.e., their implantation is reversible.

As such, a fiber with a tube configuration can be implanted in a patient and serve as a drug-eluting stent to hold a vessel or other anatomical tube open. Alternatively, fibers of the present invention may be woven or otherwise configured to form a mesh tube. In certain such embodiments, where the rigidity of the stent is responsible for maintaining a passageway or other lumen, the fibers used may be stiffer than those used in circumstances where flexibility is desired, such as with a suture that needs to be threaded through tissue. Rigidity may be increased by changing the polymer content, the manufacturing and/or curing technique, the diameter of the fiber, or the shape of the fiber (e.g., a more circular cross-section, a tubular configuration, or certain surface modifications may impart increased rigidity in the context of a mesh).

In one embodiment, a stent of the invention is loaded with the therapeutic agent heparin and employed as a coronary artery stent to hold the vessel open and elute heparin to prevent clotting. In this embodiment, a high local concentration of heparin may be delivered without causing significant systemic anticoagulation. In certain embodiments, ducts of glands may be kept open with a stent that contains an anti-scarring drug. The stents, e.g., biodegradable drug-eluting tubes, may be useful in neurological surgery, vascular surgery, urological surgery, gynological surgery, ear nose and throat surgery, or general surgery for example, whether to maintain the patency of a lumen, to permit drainage from a site of fluid build-up, or to act as a shunt through a tissue barrier. In specific embodiments, the present stents may be employed in, but not limited to, general surgery (bile system and bowel), urology (vas deferens, ureter and urethra) or gynecology (fallopian tube).

Stents of the present invention may be used in applications where traditional stents may be used. The instant stents may also contain drugs or therapeutic agents that are used in traditional stents or that may be coated on traditional stents. For example, sirolimus, paclitaxel, and estradiol, may be used with the present stents. Drugs and therapeutic agents used with the present stents may complex with one or more additives or carrier molecules, such as cyclodextrins. For example, paclitaxel may be used and complexed with one or more cyclodextrins.

Fiber of the present invention used as stents may contain one or more therapeutic agents throughout the body of the stent. Accordingly, the present stents may posses improved pharmacological properties over traditional drug-coated stents. For example, the present stents may provide increased delivery of drug and delivery over a longer duration than traditional drug-coated stents. The present stents may also provide more controllable delivery profiles. As with other fibers described herein, the pharmacological properties of the stents can be optimized and tuned for specific applications.

In another embodiment, a fiber with a tube configuration as disclosed herein may be used as a sheath to surround a traditional stent. For example, a fiber with a tube configuration may be threaded onto a traditional stent, providing a biodegradable drug-eluting layer. In some instances, the fiber may be formed directly on the stent during preparation of the fiber; thus providing a biodegradable drug-eluting coating on the stent.

The instant threads or fibers may also provide methods of treatment to patients suffering from cancer. In such embodiments, the instant polymeric thread or fiber may deliver controlled and/or sustained drug release The drug-eluting polymeric threads or fibers of the present invention may employ any polymer, or combination of polymers, described herein in addition to those appreciated by those of skill in the art. In certain embodiments, the polymeric threads or fibers employ poly(lactide-co-glycolide) (PLGA).

In certain embodiments, the fiber, threads, and/or sutures of the present invention may employ cyclodextrins (CDs) to improve the pharmacological properties of the instant systems. CDs may also be used in embodiments for treating ocular diseases or disorders, periodontal and subgingival diseases or disorders, and in nerve guide tubes. The use of CDs may improve the solubility and/or bioavailability of the therapeutic agents or drugs of the instant systems and methods. For example, certain embodiments employ ophthalmic formulations of ciprofloxacin containing hydroxypropyl-β-cyclodextrin (HPPCD, a FDA approved CD). Such complexes form inclusion complexes, and exhibit better stability, biological activity and ocular tolerance compared to ciprofloxacin alone (Nijhawan and Agarwal, 2003). Also, these CD-containing solutions may not lead to ocular ciprofloxacin precipitation because of the greatly increased solubility of the inclusion complexes over the drug alone. Corneal ciprofloxacin precipitation may delay epithelial healing (Wilhelmus and Abshire, 2003). In some embodiments, CD:drug inclusion complexes can be formed at ambient temperature and collected. In certain embodiments, the therapeutic agent or drug is interacting with the interior of the CD cup, and the exterior of the CD cup may provide the interface to the polymer. In these embodiments, a three-component system (polymer, CD, drug) can be combined in solution for wet-spinning to occur, for formation of the drug-eluting fiber. Since CDs can form inclusion complexes with many different drugs (over 30 different products worldwide; Davis and Brewster, 2004), the instant methods and systems have general application to drug delivery.

While certain embodiments contemplate the use of a thread or fiber comprising cyclodextrin complexes and a single drug, such as an antibiotic or a corticosteroid, other embodiments may contemplate a suture that employs multiple drug combinations, for example, a suture that comprises CD complexes, an antibiotic, and a corticosteroid. To illustrate, some embodiments may comprise TobraDex®, an ophthalmic ointment that contains an antibiotic (tobramycin), and a corticosteroid (dexamethasone) to suppress an inflammatory response. The combination of an antibiotic and a corticosteroid may be contained in the drug-eluting suture by first preparing inclusion complexes of the two drugs with CDs and then adding both to the polymer for wet-spinning of the fiber. In some embodiments, the drugs are FDA approved. In yet further embodiments, all components of the drug-eluting suture have FDA approval.

All patents, publications, and references cited in the foregoing disclosure are expressly incorporated herein by reference. The following references are expressly incorporated herein: Aminabhavi, T. M., Yenkar, P. S. and Kulkarni, A. R. (2003) Polymers in Drug Delivery: Bioresponsive Polymers in Ophthalmic Delivery of Drugs. *Polymer News* 28, 150-153; Arnold, R. K. (1977) Ocular drug delivery device. U.S. Pat. No. 4,014,335; Babu, M. K. M., Thompson, R. P. and Godiwalla, T. N. (2004) Ciprofloxacin formulations and methods of making and using the same. U.S. patent application 2004/020687; Barbolt, T. A. (2002) Chemistry and Safety of Triclosan, and Its Use as an Antimicrobial Coating on Coated VICRYL Plus Antibacterial Suture (Coated Polyglactin 910 Suture with Triclosan). *Surgical Infections* 3, S45-S53; Baeyens, V., Felt-Baeyens, O., Rougier, S., Pheulpin, S., Boisrame, B. and Gurny, R. (2002) Clinical evaluation of bioadheisve ophthalmic drug inserts (BODI (R)) for the treatment of external ocular infections in dogs. *J. Control. Release* 85, 163-168; Blanchemain et al. (2005) Vascular PET Prostheses Surface Modification with Cyclodextrin Coating: Development of a New Drug Delivery System. *Eur. J. Vasc. Endovsc. Surg.* 29, 628-632. Brewster, M. E., Verreck, G., Chun, I., Rosenblatt, J., Mensch, J., Van Dijck, A., Noppe, M., Ariën, A., Bruining, M. and Peeters, J. (2004) The use of polymer-based electrospun nanofibers containing amorphous drug dispersions for the delivery of poorly water-soluble pharmaceuticals. *Pharmazie* 59, 387-391; Brown, M. M., Brown, G. C. and Spaeth, G. L. (1984) Improper topical self-administration of ocular medication among patients with glaucoma. *Can. J. Ophthalmology* 19, 2-5; Buchenska, J., Slomkowski, S., Tazbir, J. W. and Sobolewska, E. (2001) Poly(ethylene terephthalate) yarn with antibacterial properties. *J. Biomat. Sci.-Polym. E.* 12, 55-62; Chandavarkar, M. A., Chandavarkar, N. M. and Chandrashekhar, M. (2004) Combination drug. U.S. patent application 2004/0077562; Chao, J., Chen, L., Xu, H. and Meng, D. (2002) Preparation and study on the solid inclusion complex of ciprofloxacin with β-cyclodextrin. *Spectrochim. Acta A* 58, 2809-2815; Chao, J., Meng, D., Li, J., Xu, H. and Huang, S. (2004) Preparation and study on the novel solid inclusion complex of ciprofloxacin with HP-β-cyclodextrin. *Spectrochim. Acta A* 60, 729-734; Charoo N A, Kohli K, Ali A, Anwer A. (2003) Ophthalmic delivery of ciprofloxacin hydrochloride from different polymer formulations: in vitro and in vivo studies. *Drug Dev Ind Pharm.* 29(2), 215-221; Chiang, C.-H., Tung, S.-M., Lu, D.-W. and Yeh, M.-K. (2001) In Vitro and In Vivo Evaluation of an Ocular Delivery System of 5-Fluorouracil Microspheres. *J. Ocul. Pharmacol. Ther.* 17, 545-553; Chkhikvadze, T. F., Kokhodze, D. N. and Dzhikiya, D. T. (1991) Novel antimicrobial absorbable sutures for gastrointestinal surgery. *Soobshch. Akad. Nauk. Gruz. SSSR* 131, 417-420; Davis, M. E. and Brewster, M. E. (2004) Cyclodextrin-based pharmaceutics: past, present, future. *Nat. Rev. Drug Deliv.* 3, 1023-1035; Di Colo, G., Burgalassi, S., Chetoni, P., Fiaschi, M. P., Zambito, Y. and Saettone, M. F. (2001) Relevance of polymer molecular weight to the in vitro/in vivo performances of ocular inserts based on poly(ethylene oxide). *Int. J. Pharm.* 220, 169-177; Di Colo, G. and Zambito, Y. (2002) A study of release mechanisms of different ophthalmic drugs from erodible ocular inserts based on poly(ethylene oxide). *Eur. J. Pharm. Biopharm.* 54, 193-199; Friedrich, S. W., Saville, B. A., Cheng, Y. L. and Rootman, D. S. (1996) Pharmacokinetic differences between ocular inserts and eyedrops. *J. Ocul. Pharmacol. Ther.* 12, 5-18; Giannavola, C., Bucolo, C., Maltese, A., Paolino, D., Vandelli, M. A., Puglisi, G., Lee, V. H. L. and Fresta, M. (2003) Influence of Preparation Conditions on Acyclovir-Loaded Poly-d,l-Lactic Acid Nanospheres and Effect of PEG coating on Ocular Drug Bioavailability. *Pharm. Res.* 20, 584-590; Green L C, Callegan M C, Engel L S, Shimomura Y, Jasheway D W, O'Callaghan R J, Hill J M. (1996) Pharmacokinetics of topically applied ciprofloxacin in rabbit tears. *Jpn J Ophthalmol.* 40(1), 123-126; Gurtler, F. and Gurny, R. (1998) Bioadhesive ophthalmic insert. U.S. Pat. No. 5,773,021; Huang, L., Taylor, H., Gerber, M., Orndorff, P. E., Horton, J. R. and Tonelli, A. (1999) Formation of Antibiotic, Biodegradable/Bioabsorbable Polymers by Processing with Neomycin Sulfate and Its Inclusion Compound with β-Cyclodextrin. *J. Appl. Polym. Sci.* 74, 937-947; Ignatious, F. and Baldoni, J. M. (2001) Electrospun pharmaceutical compositions comprising a polymeric carrier. WO 0154667; Jain, R. A. (2000) The manufacturing techniques of various drug loaded biodegradable poly(lactide-co-glycolide) (PLGA) devices. *Biomaterials* 21, 2475-2490; Kato, A., Kimura, H., Okabe, K., Okabe, J., Kunou, N. and Ogura, Y. (2004) Feasibility of Drug Delivery to the Posterior Pole of the Rabbit Eye with an Episcleral Implant. *Invest. Ophth. Vis. Sci.* 45, 238-244; Kinane et al. (1999) A Six-Month Comparison of Three Periodontal Local Antimicrobial Therapies in Persistent Periodontal Pockets. *Periodontal* 70, 1-7; Konstas, A. G. P., Maskaleris, G., Gratsonidis, S. and Sardelli, C. (2000) Compliance and viewpoint of glaucoma patients in Greece. *Eye* 14, 752-756; Kurtz, L. D. (1975) Sutures having long-lasting germicidal properties. U.S. Pat. No. 3,862,304; Limberg M, Bugge C. (1994) Tear concentrations of topically applied ciprofloxacin. *Cornea* 13(6), 496-499; Loftsson, T., Fridriksdottir, H., Sigurdardottir, A. M. and Ueda, T. (1994) The effects of water-soluble polymers on drug-cyclodextrin complexation. *Int. J. Pharm.* 110, 169-177; Loftsson, T. and Järvinen, T. (1999) Cyclodextrins in ophthalmic drug delivery. *Adv. Drug Del. Rev.* 36, 59-79; Loftsson, T. and Másson, M. (2004) The effects of water-soluble polymers on cyclodextrins and cyclodextrin solubilization of drugs. *J. Drug Del. Sci. Tech.* 14, 35-43; Lu, J., Hill, M. A., Hood, M., Greeson, Jr., D. F., Horton, J. R., Orndorff, P. E., Herndon, A. S. and Tonelli, A. E. (2001) Formation of Antibiotic, Biodegradable Polymers by Processing with Irgasan DP300R (Triclosan) and Its Inclusion Compound with β-Cyclodextrin. *J. Appl. Polym. Sci.* 82, 300-309; MacNeill et al. (1998) The Time and Ease of Placement of the Chlorhexidine Chip Local Delivery System. *Compendium* 19, 1158-1167; Nagaraju, R., Udupa, N., Mathew, J. and Varma, B. R. R. (1999) Biodegradable dental implants of ciprofloxacin β-cyclodextrin inclusion complex in the treatment of periodontitis. *Indian J. Exp. Biol.* 37, 305-307; Nelson, K. D., Romero, A., Waggoner, P., Crow, B., Borneman, A. and Smith, G. M. (2003) Technique Paper for Wet-Spinning Poly(L-lactic acid) and Poly(DL-lactide-co-glycolide) Monofilament Fibers. *Tissue Eng.* 9, 1323-1330; Nijhawan, R. and Agarwal, S. P. (2003) Development of an ophthalmic formulation containing Ciprofloxacin-Hydroxypropyl-b-Cyclodextrin complex. *Boll. Chim. Farmac.* 142, 214-219; Okimoto, K., Miyake, M., Ohnishi, N. Rajewski, R. A., Stella, V. J., Irie, T. and Uekama, K. (1998) Design and Evaluation of an Osmotic Pump Tablet (OPT) for Prednisolone, a Poorly Water Soluble Drug, Using $(SBE)_{7m}$-β-CD. *Pharm. Res.* 15, 1562-1568; Rusa, C. C., Shuai, X., Shin, I. D., Bullions, T. A., Wei, M., Porbeni, F. E., Lu, J., Huang, L., Fox, J. and Tonelli, A. E. (2004) Controlling the Behaviors of Biodegradable/Bioabsorbable Polymers with Cyclodextrins. *J. Polym. Environ.* 12, 157-163; Saishin, Y., Silva, R. L., Saishin, Y., Callahan, K., Schoch, C., Ahlheim, M., Lai, H., Kane, F., Brazzell, R. K., Bodmer, D. and Campochiaro, P. A. (2003) Periocular Injection of Microspheres Containing PKC412 Inhibits Choroidal Neovascularization in a Porcine Model. *Invest. Ophth. Vis. Sci.* 44, 4989-4993; Sasaki, H., Nagano, T., Sakanaka, K., Kawakami, S., Nishida, K., Nakamura, J., Ichikawa, N., Iwashita, J., Nakamura, T. and Nakashima, M. (2003) One-side-coated insert as a unique ophthalmic drug delivery system. *J. Control. Release* 92, 241-247; Singh, O. N. and Bhagat, H. G. (2001) Topical suspension formulations containing ciprofloxacin and dexamethasone. U.S. Pat. No. 6,284,804; Smith, T. J., Ashton, P. and Pearson, P. A. (1995) Sustained release drug delivery devices. U.S. Pat. No. 5,378,475; Smith, T. J. and Ashton, P. (1996) Sustained-Release Subconjunctival 5-Fluoroacil. *Ophthalmic Surg. Las.* 27, 763-767; Spooner, J. J., Bullano, M. F., Ikeda, L. I., Cockerham, T. R., Waugh, W. J., Johnson, T. and Mozaffari, E. (2002) Rates of discontinuation and change of glaucoma therapy in a managed care setting. *Am. J. Manag. Care* 8, S262-S270; Storch, M., Scalzo, H., Van Lue, S. and Jacinto, G. (2002) Physical and Functional Comparison of Coated VICRYL Plus Antibacterial Suture (Coated Polyglactin 910 Suture with Triclosan) with Coated VICRYL Suture (Coated Polyglactin 910 Suture). *Surgical Infections* 3, S65-S77; Tan, D. T. H., Chee, S.-P., Lim, L. and Lim, S. M. (1999) Randomized Clinical Trial of a New Dexamethasone Delivery System (Surodex) for the Treatment of Post-Cataract Surgery Inflammation. *Ophthalmology* 106, 223-231; Velez, G. and Whitcup, S. M. (1999) New developments in sustained release drug delivery for the treatment of intraocular disease. *Brit. J. Ophthamol.* 83, 1225-1229; Verreck, G., Chun, I., Peeters, J., Rosenblatt, J. and Brewster, M. E. (2003a) Preparation and Characterization of Nanofibers Containing Amorphous Drug Dispersions Generated by Electrostatic Spinning. *Pharm. Res.* 20, 810-817; Verreck, G., Chun, I., Rosenblatt, J., Peeters, J., Van Dijck, A., Mensch, J., Noppe, M. and Brewster, M. E. (2003b) Incorporation of drugs in an amorphous state into electrospun nanofibers composed of a water-insoluble, nonbiodegradable polymer. *J. Control. Release* 92, 349-360; Weyenberg W, Vermeire A, Dhondt M M, Adriaens E, Kestelyn P, Remon J P, Ludwig A. (2004) Ocular bioerodible minitablets as strategy for the management of microbial keratitis. *Invest Ophthalmol Vis Sci.* 45(9), 3229-3333; Wilhelmus, K. R. and Abshire, R. L. (2003) Corneal ciprofloxacin precipitation during bacterial keratitis. *Am. J. Ophthalmol.* 136, 1032-1037.

EXAMPLES

The invention now being generally described, it will be more readily understood by reference to the following examples which are included merely for purposes of illustration of certain aspects and embodiments of the present invention, and are not intended to limit the invention.

1. Preparation of Drug-Cyclodextrin Inclusion Complexes

Solid inclusion complexes of ciprofloxacin with hydroxypropylated-β-cyclodextrin (HP-β-CD), randomly methylated-β-cyclodextrin (RM-β-CD), and sulfobutylether-β-cyclodextrin (SBE-β-CD) were prepared. For each formulation, approximately 0.2 g of ciprofloxacin was mixed with 50 g of water and acidified with drops of 2 M HCl to pH 3 to dissolve the ciprofloxacin. Cyclodextrin, in either a 1:1 or 2:1 molar cyclodextrin to ciprofloxacin ratio, was added to the stirred solution. The solution remained stirring overnight. The product was then freeze-dried to give a solid, light yellow lyophilized powder. Ciprofloxacin-HCl was made as a control by acidifying ciprofloxacin and freeze-drying the product without the addition of cylcodextrin. The exact formulations are shown in Table 1.

TABLE 1

| Cyclodextrin Type | Cyclodextrin: Ciprofloxacin | Mass Cyclodextrin (gm) | Mass Ciprofloxacin (gm) |
|---|---|---|---|
| Hydroxypropylated-β | 2:1 | 3.1864 | 0.3994 |
| Hydroxypropylated-β | 1:1 | 0.8043 | 0.2011 |
| Randomly Methylated-β | 2:1 | 1.6684 | 0.2013 |
| Sulfobutylether-β | 1:1 | 1.5987 | 0.1967 |

2. Preparation of a Drug-Eluting Fiber—Method A

Generally, PLGA was dissolved in dimethylformamide (DMF) and the solution wet-spun into a water coagulation medium (polymer coagulates in water to produce the fiber) at ambient temperature. For drugs that are not soluble in DMF or the polymer (like ciprofloxacin), the wet-spinning method may not provide highly consistent results where the polymer and drug are simply physically mixed together. Cyclodextrins (CDs) can be employed in such circumstances to overcome this difficulty by forming inclusion complexes with the drug. For example, ciprofloxacin has been used with very good results in the treatment of microbial ophthalmic infections in the form of eye drops at a concentration of 0.3% wt/v.

A laboratory-scale wet-spinning machine was constructed and is shown in FIG. 5a. The small size of the apparatus permits preparation of numerous variations of the fibers without consuming large quantities of the drugs.

PLGA (50% lactic acid:50% glycolic acid) was purchased from Boehringer Ingelheim Chemicals (Indianapolis, Ind.). RG506 PLGA has an average molecular weight of 98,000 kDa. Nelson et al. (2003) dissolved PLGA in chloroform (15 wt %) to give a very viscous, clear solution. This solution was wet-spun into fiber using isopropanol as the coagulation fluid. It was found that this combination of solvents gives gels with PLGA that are difficult to process. Because of this, a new formulation for the wet spinning of PLGA was developed. Using water as the coagulation medium 33 wt % PLGA in DMF produced improved fibers. The PLGA:DMF solutions of the instant invention are less viscous than the PLGA: chloroform mixtures. FIG. 5a shows the wet-spinning apparatus when it is actually spinning fiber, and FIG. 5b shows the take-up bobbin holding 5 meters of 0.4 mm diameter PLGA fiber that was spun using the instant methodology. A white fiber is desirable in certain applications for cosmetic reasons.

RMβCD and HPβCD were purchased from CYCLOLAB and SBEβCD was obtained as a gift from CyDex. As an example, the PLGA fiber that contains ciprofloxacin:RM-βCD complexes was prepared. RMβCD and PLGA are soluble in DMF while ciprofloxacin is not. Inclusion complexes of ciprofloxacin and RMβCD were prepared by freeze-drying an aqueous solution containing both molecules to give a white powder. The infrared (IR) spectrum of the solid showed the presence of both the ciprofloxacin and the RMβCD. To prove that the solid contained inclusion complexes and was not just a physical mixture of the two components, differential scanning calorimetry (DSC) was used. The DSC data showed an intense endothermic peak at 544 K for the ciprofloxacin while its physical mixture with the RMβCD shifts this peak to 516 K. The solid collected from the freeze-drying showed a peak at 507 K indicating that the powder is not a physical mixture of the two components but rather inclusion complexes. Additionally, when the physical mixture was placed in DMF and the PLGA added, the solution contained a suspension of the ciprofloxacin (by comparison to addition to ciprofloxacin in DMA and PLGA) while the combination of the inclusion complex with DMF and PLGA gave a clear solution like was observed with the DMF and PLGA alone. In FIG. 6, solutions containing DMF and PLGA (at 33 wt %) are shown. Solution (a) is with RMβCD, (b) contains a physical mixture of RMβCD and ciprofloxacin and (c) has the inclusion complexes of RMβCD and ciprofloxacin. Note that the physical mixture is not a clear solution (mixtures of DMF, PLGA and ciprofloxacin appear like this; not shown), while the inclusion complexes are dissolving to give a clear solution.

Two fibers were prepared: (i) PLGA alone and (ii) PLGA+ RMβCD:ciprofloxacin inclusion complexes. The fibers prepared according to Method A are shown in FIG. 7a. The antibacterial activity of the ciprofloxacin-containing fibers was investigated in vitro by placing them in contact with DH5-alpha *E. coli* grown on LB agar plates at 37° C. in an incubator. FIG. 8 illustrates the bacterial plates containing fibers.

3. Preparation of a Drug-Eluting Fiber—Method B

Polymer formulations containing the HCl salt of ciprofloxacin as well as the ciprofloxacin inclusion complexes with cyclodextrins were made as follows. First, the active agent was dissolved in 1.5 g of DMSO in a 4 mL vial on a shaker table at 50° C. The active agent contained approximately 17-18 mg of ciprofloxacin when cyclodextrin was present and 15 mg of ciprofloxacin if the HCl salt was used. This difference was due to the salt not being as soluble in DMSO, especially when polymer is present. Approximately 0.35 g of 50:50 poly(lactic-co-glycolic acid) (PLGA) was added to the vial and homogenized by vortexing. In the case of SBE-β-CD-Ciprofloxacin complex, small amounts of DMSO were added to prevent phase separation. The formulation was again placed on the heated shaker until bubbles formed during the dissolution of the polymer settled out of the solution. Each solution was a translucent yellow color and not turbid to the naked eye, indicating dissolution of both the ciprofloxacin and PLGA. A 5 mL syringe was loaded with 1 mL of the polymer solution. A fiber was then extruded through a 23 gauge needle at 250 µl/min into the coagulation fluid. The coagulation fluid was 75:25 2% sodium dodecyl sulfate (SDS):isopropanol. The coagulation fluid was stirred continuously to prevent a build up of dimethylsulfoxide in the vessel. The fibers were allowed to coagulate for 10 min in the fluid and were then removed and dried by hanging overnight. The fibers had a reliably consistent diameter of 0.4 mm. FIG. 7b depicts a close-up view of the fibers prepared according to Method B, The fibers shown in FIG. 7b contain inclusion complexes of HPβCD and ciprofloxacin and illustrate the fiber diameter of approximately 0.4 mm. The exact fiber formulations are shown in Table 2.

Coagulation Fluid: 75:25 2% SDS in Water:Isopropanol

TABLE 2

| Active Agent | Active Agent Mass (gm) | Mass Ciprofloxacin (gm) | Mass DMSO (gm) | Mass PLGA (gm) |
|---|---|---|---|---|
| 2:1 HP-β-CD:Ciprofloxacin | 0.1533 | 0.0170 | 1.4902 | 0.3548 |
| 1:1 HP-β-CD:Ciprofloxacin | 0.0845 | 0.0169 | 1.5108 | 0.3565 |
| 1:1 SBE-β-CD:Ciprofloxacin | 0.1539 | 0.0171 | 2.0141 | 0.3561 |
| 2:1 RM-β-CD:Ciprofloxacin | 0.1535 | 0.0171 | 1.4999 | 0.3534 |
| Cipro-HCl | 0.0147 | 0.0147 | 1.5048 | 0.356 |

Drug loading of each fiber was measured by high performance liquid chromatography (HPLC). First, 6 inches of fiber was digested with 0.5 mL of 1 M NaOH for 1 hr on a shaker. Then, the excess base was neutralized with 1 M HCl and 3 mL of 0.1% trifluoroacetic acid (TFA) in water was added to the solution. Samples were loaded on to the HPLC with a mobile phase of 50:50 0.1% TFA in water:0.1% TFA in acetonitrile and a C18 column. The concentration of ciprofloxacin in the solution was determined and the amount of ciprofloxacin per inch was calculated. The results are summarized in FIG. 9, where it is shown that increased loadings of drug into the fibers can be achieved through the formation of drug-cyclodextrin inclusion complexes. A higher cyclodextrin:drug ratio may effect increased levels of drug loading.

4. Coagulation Fluid Study

Several different coagulation fluids were tested to determine the relative effectiveness. Polymer solutions were prepared by mixing 0.15 g 2:1 HP-β-CD:ciprofloxacin, 1.5 g DMSO, and 0.35 g PLGA for 3 hours at 50° C. Fibers were then extruded through a 23 gauge, flat-tipped needle into 40 mL of water, 2% SDS in water, or 75:25 2% SDS in water:isopropanol. After 10 min of coagulation, the fibers were hung to dry overnight. After drying, 6 inches of fiber were digested with 0.5 mL of 1 M NaOH. Then, the excess base was neutralized with 1 M HCl and 3 mL of 0.1% trifluoroacetic acid (TFA) in water was added to the solution. Samples were loaded on to the HPLC with a mobile phase of 50:50 0.1% TFA in water:0.1% TFA in acetonitrile and a C18 column. The concentration of ciprofloxacin in the solution was determined and the amount of ciprofloxacin per inch was calculated. The results are summarized in FIG. 10, where it is shown that significant improvements in drug loading can be achieved by including a surfactant, such as SDS, in the coagulation fluid, For example, using a surfactant allowed an increase from approximately 1.5 µg drug/inch fiber in water to approximately 8 µg drug/inch fiber in 2% SDS in water. Moreover, the coagulation fluid can be tuned to provide a further increase in drug loading by the addition of a polar organic solvent, such as an alcohol like isopropanol. For example, the change in fluid permitted an increase from approximately 8 µg drug/inch fiber in 2% SDS in water to approximately 20 µg drug/inch fiber in 2% SDS in 75:25 water:isopropanol.

5. Preparation of a Drug-Eluting Bulb

A polymer solution containing 0.15 g 2:1 HP-β-CD/ciprofloxacin, 1.5 g DMSO, and 0.35 g PLGA was made. Approximately 0.5 mL of polymer solution was drawn into a 1 mL slip-tip syringe. Slowly, the syringe plunger was depressed in open air, allowing drops of polymer solution to form on the tip. The drops were collected in a stirring solution of 75:25 2% SDS in water:isopropanol and allowed to coagulate for 2 hours. The solidified bulbs were then collected from the solution and their dimensions were measured with calipers. The bulbs were uniformly 3.3 mm wide and 4.3 mm long, with a thin tail extending a further 2-7 mm. The bulbs all had masses between 21-23 mg 20 minutes after removal from the coagulation fluid. Bulbs were digested with 1 M NaOH and analyzed for drug content by HPLC. The drug loading of these bulbs was measured to be 141±11 µg ciprofloxacin/bulb. FIG. 11a depicts a photograph of a drug-eluting bulb with a tail section. Bulbs were also modified by removing the small tail with a razor. Then, the bulb was attached to a 0.4 mm diameter PLGA fiber by bringing the fiber and bulb into contact and fusing them together with a small amount of acetone. FIG. 11b depicts a photograph of a drug-eluting bulb fused to a fiber of the present invention.

6. Preparation of a Drug-Eluting Nerve Guide Tube

A PLGA solution containing ciprofloxacin was made by dissolving 0.15 g 2:1 HP-β-CD:ciprofloxacin and 0.35 g PLGA in 1.5 g of DMSO. The tube was made by a simple dip-coating procedure where a 22 gauge flat-tipped needle acted as the mandrel. The needle was submerged in the polymer solution and slowly drawn up out of the solution. The polymer-coated needle was quickly submerged in 75:25 2% SDS in water:isopropanol to coagulate. After 10 minutes, the needle was removed from the coagulation fluid. The tube was carefully cut at the top and bottom and gently slid from the needle. The inner diameter of the fiber was 0.75 mm while the wall thickness was about 0.1 mm. From the tube, 1 cm was removed and digested with 1 M NaOH. This sample was then analyzed by HPLC to get a tube wall loading of 36 µg/inch. FIG. 12a shows the drug-eluting nerve guide tube on the mandrel. FIG. 12b depicts the nerve guide tube after removal from the mandrel.

7. Physical Characterization of Fibers

Solid-state NMR studies may be performed on the fibers obtained to give quantitative amounts of polymer, drug and CD present. Complete dissolution of the fibers gives solutions that can be analyzed by high-performance liquid chromatography (HPLC) methods for the drugs (see for example Babu et al., 2004 for a HPLC method of analyzing ciprofloxacin), CDs, and any small amounts of residual DMF or DMSO. CDs are analyzed by NMR and HPLC (using the appropriate detectors, such as evaporative light scattering). The combination of the two methods provides for confirmation of the composition. The mechanical properties of the fibers is also being evaluated. Properties such as tensile strength are measured and compared to commercial sutures.

8. Dissolution Studies of Fibers

The fibers are investigated as follows. Fibers are placed in phosphate-buffered saline (PBS) in the presence and absence of human serum. The fibers are exposed to these solutions at 37° C. for specified times and recovered. The mass of the fiber remaining is recorded and the amount of CD and drug in solution quantified by HPLC. These results provide the dissolution profile for the fiber and the release rates of the drugs and CDs. For some time points, the remaining fibers are tested for mechanical strength. That way, the mechanical properties can be monitored as the fibers dissolve.

9. Testing of the Drug-Eluting Fibers in Vitro

The antibacterial activity of the ciprofloxacin-containing fibers is investigated in vitro. DH5-alpha *E. coli* are grown on LB agar plates at 37° C. in an incubator. FIG. 8 illustrates the bacterial plates containing fibers. The growth of the bacteria in the presence of the fibers is monitored and the reduction in growth is used as an indicator of active release of ciprofloxacin.

10. Plan for Testing of the Drug-Eluting Fibers In Vivo

The fibers prepared and characterized herein are tested in vivo using the rabbit as the animal model. The in vivo study evaluates the:

1) Drug-eluting characteristics of the suture
2) Drug bioavailability to the aqueous fluid
3) Suture longevity
4) Tissue reaction to the suture Each rabbit has bilateral suture implants, one eye receiving a drug-eluting suture, and the other eye a control suture without drug (i.e., VICRYL (polyglactin 910; PLGA)). Rabbits are examined, eyes photographed, and tear samples taken at various intervals per the study protocol described below. At the end of the study, intraocular aqueous fluid is sampled and tissue from the implantation site surgically biopsied. There are 12 rabbits used in this study. They are divided into 4 groups, each group having a different study duration: 1 week, 2 weeks, 4 weeks and 8 weeks. The study durations are based on the clinical dissolution rates of 6-0 VICRYL suture. The number of rabbits was determined after review of the literature and based on the premise to use as few rabbits as possible yet obtain meaningful data.

Study Groups:

Study 1: Group 1=1 week duration, 3 rabbits, Group 2=2 weeks duration, 3 rabbits Study 2: Group 3=4 weeks duration, 3 rabbits, Group 4=8 weeks duration, 3 rabbits Study 1 investigates the short term properties of the suture and will involves groups 1 and 2 using a total of 6 rabbits for a maximum of 2 weeks. Study 1 data is analyzed prior to proceeding to Study 2. The research study team addresses problems with sutures, sampling intervals, or the protocol prior to going to Study 2.

Study 2 is longer term involving groups 3 and 4 using a total of 6 rabbits with a duration of 4 to 8 weeks. The protocol is the similar to that used in Study 1 with modifications of sample intervals or suture based on Study 1 data.

The rabbit is the animal of choice for most studies on ocular pharmacokinetics because of its similarity to humans in ocular structure. Animal studies may be performed with approval and oversight of a research animal committee and a laboratory veterinarian. The care and treatment of the rabbits may be monitored by the laboratory veterinarian to assure humane treatment of the rabbits.

1) Drug-eluting characteristics of the suture. The drug-eluting characteristics of the sutures are determined by sampling tears from each eye of the rabbit before and after suture implantation. Tears are extracted from the rabbit's conjunctival fornix using a capillary tube micro-pipette. Mild sedation is used to calm the rabbits for tear extraction which is non-traumatic and not painful. Tears are analyzed for drug concentrations using a validated HPLC techniques. On the day of implantation, tear samples are obtained at 30 min, 60 min, 120 min, and 300 min after implantation. After the first day, samples are collected every day for two weeks, then on every third day until the termination of the study as per each individual study group as described above. Time intervals for sampling were determined by review of the previous studies on the pharmacokinetics of topical drugs and drug concentrations in the tear film (Limberg and Bugge, 1994; Green et al., 1996; Weyenberg et al. 2004). Study 2 sampling intervals maybe modified based on Study 1 findings.

For all drug testing the laboratory is masked as to the eye being sampled. During data analyses, the data are masked from the researcher as to eye sampled and time when the sample was obtained.

2) Drug bioavailability to the aqueous fluid. The drug bioavailability to the aqueous fluid of the anterior chamber is assessed by sampling the aqueous fluid and then measuring the drug concentration by HPLC. Aqueous drug concentrations are compared to tear drug concentrations taken at the same time to determine the drug diffusion gradient across the cornea to the anterior chamber. Sampling of aqueous fluid requires an anterior chamber tap. This is a procedure where the cornea is penetrated with a micro-needle to gain access to the aqueous fluid. Because this is a delicate and invasive procedure, systemic anesthesia with topical anesthesia is used. The anterior chamber tap is only performed once for each rabbit at the end of the study. The duration of the study depends on the individual study group as described above For all drug testing the laboratory is masked as to the eye being sampled. During data analyses, the data are masked from the researcher as to eye sampled and time when the sample was obtained.

3) Suture longevity. The longevity of the suture and rate of suture absorption is determined by measurements obtained from photographs, direct measurements with a caliper, and histological measurements taken from biopsies. Photographs and caliper measurements are obtained at the time of implantation and each week until the end of the study. Mild sedation can be used to calm the rabbits for examination and photographs, which are non-invasive and not painful. At the end of the study, a biopsy of the suture area is taken and the suture diameter measured using systemic anesthesia and topical anesthesia. The photography is further explained below. Examiners are masked as to when the photographs were taken, and to which eye was photographed.

4) Tissue reaction to the suture. Ocular and peri-ocular tissue reaction from suture implantation is evaluated by:

a) Clinical exams
b) Comparison of serial photographs
c) Histological examination of implant site a) Clinical exams. Clinical assessment includes direct observation of the eye and conjunctiva under magnification using the direct ophthalmoscope. Clinical ratings are performed prior to suture implantation and at each week subsequent until the study ends for each individual group. A trained technician documents the intervening weekly clinical ratings. Examinations are not painful and do not cause discomfort, but may cause stress so they can be done with mild sedation using Ketamine.

Using a clinical rating of 0-4 (with 0 being normal and 4 being abnormal or presence of a severe injection), the following anatomical areas are evaluated: inferior fornix conjunctiva area of implantation, anterior chamber, superior fornix conjunctiva, iris and pupil, inferior bulbar conjunctiva, lens, superior bulbar conjunctiva, red reflex (retina and vitreous), and cornea.

b) Comparison of serial photographs. A digital camera is used to obtain serial photographs before suture implantation and at predetermined staggered intervals after impanation: immediately after implantation then every week for the duration of the study. Photographs are taken without flash under identical lighting conditions for each examination. Photography without flash does not cause discomfort but may cause stress, so photography can be done with mild sedation at the discretion of the veterinarian. The working distance, camera, and camera settings are the same for each examination producing a picture close to a 1:1 ratio.

Two masked observers evaluate photographs for the first 7 areas as per the clinical rating system described above. Anatomical areas lens and red reflex, are excluded as they may not show well on external photographs.

Examiners are masked to when the photographs were taken and to which eye is photographed.

c) Histological examination of implant site. A tissue biopsy from the implantation site is obtained at the end of the study for each study group. The surgical biopsy are done while the rabbit is under systemic anesthesia and after administering topical anesthesia. After biopsy, the specimen is immediately placed in formaldehyde fixative for transport. The tissue specimen is sent to an ocular pathology laboratory for pathological evaluation and H&E staining. Additional stains are done at the discretion of the pathologist. The diameter of the remaining suture is measured and recorded for each rabbit.

The pathologist is masked as to the eye being sampled and to the study group.

5) Suture implantation, technique and randomization. The sutures are implanted in the inferior conjunctival fornix. Systemic anesthesia along with topical anesthesia as described below is used so the rabbits have no pain or discomfort. The procedure of suture implantation is minimally invasive and in humans conjunctival suturing is done with topical anesthesia alone patient full awake.

Suture implantation is achieved by connecting the suture to a surgical needle and passing the needle through the conjunctiva into the sub-conjunctival space. The suture is dragged into the sub-conjunctival space. The excess suture on the surface is cut close to the surface of the conjunctiva leaving the sub-conjuntival suture in place. The length of suture left in the sub-conjunctival space is approximately 7 mm. This is a simple procedure and is not associated with postoperative pain as the suture is covered by the conjunctiva.

Eyes are randomized by a coin flip to:
Heads=Right eye drug suture; Left eye control VICRYL suture
Tails=Left eye drug suture; Right eye control VICRYL suture If 2 out of 3 rabbits in a study group are randomized so the drug-eluting suture is on the same side then the last rabbit in that study group has the drug suture placed in the opposite eye. This is to keep the distribution of drug-eluting suture somewhat balanced between right and left eyes.

6) Data Analyses

Drug-eluting characteristics of the suture. Tear film concentrations of drug from the drug-eluting suture test eye and the control suture eye are compared for time specific samples. A tear film drug concentration curve is created. In the case of ciprofloxacin, tear film concentrations are also compared to the minimum inhibitory concentrations (MIC) for 90% of strains commonly reported for a majority of potential pathogens in tear film (Limberg and Bugge, 1994). Ciprofloxacin tear film concentrations of 1.5 micrograms/mL or greater are considered clinically adequate for antibiotic treatment. The onset and duration of adequate ciprofloxacin concentrations in the tear film are analyzed. This analysis determines the onset and duration of clinically adequate drug concentrations in the tears delivered by the implanted drug-eluting suture.

Drug bioavailability to the aqueous fluid. Drug bioavailability to the aqueous fluid of the anterior chamber is analyzed by comparing tear concentrations of drug to aqueous fluid concentrations taken at the same time. This analysis gives a conjunctival-to-corneal permeability ratio. Aqueous fluid concentrations for ciprofloxacin are plotted over time, and compared to MIC 90 for common ocular pathogens. This analysis identifies appropriate drug concentrations needed to provide adequate intraocular drug concentrations. Aqueous fluid antibiotic concentrations are important in preventing postoperative infections after intraocular surgery.

Suture longevity. Suture longevity data is compared to the tear film drug concentration curve to identify a relationship of suture size, and suture duration, to tear film drug concentrations. It is expected that as the suture dissolves and shrinks in size over time that there is a corresponding reduction in tear drug concentrations. This analysis is used to develop the appropriate suture size to deliver clinically adequate drug therapy.

Tissue reactions to the suture. Comparative analysis of data on drug-eluting suture vs. control suture for, (i) clinical examination, (ii), eye photographs, and (iii) histological studies is made to identify possible adverse effects of the drug suture. This analysis evaluates the biocompatibility of the drug-eluting suture.

7) Summary of Study Protocol
1. Pre-implant work-up:
   (a) Clinical rating; (b) measurement of sutures; (c) photograph of eyes; (d) tear sample of each eye
2. Day 1—randomization and implantation:
   (a) Implant sutures; (b) measurement of implanted sutures; (c) photograph of implanted sutures; (d) tear samples taken at 30 min, 60 min, 120 min and 300 min
3. Days 2-14:
   (a) Daily tear samples; (b) weekly clinical rating; (c) weekly photograph; (d) weekly suture measurement
4. Day 15 to end of study for each group:
   (a) Every other day tear samples; (b) weekly clinical rating; (c) weekly photograph; (d) weekly suture measurement
5. Last study day for each group for:
   (a) Tear sample; (b) clinical rating; (c) photograph; (d) suture measurement; (d) anterior chamber tap for aqueous fluid; (f) excisional biopsy of suture implant site 11. Testing of the Drug-Eluting Fibers In Vivo 1) Fiber production. Fibers were produced by a wet-spinning technique analogous to Method B described above. Briefly, polymer solution consisting of 0.30 g 2:1 HP-β-CD:ciprofloxacin, 0.70 g PLGA, and 3.0 g DMSO was extruded through a 23 gauge needle into 75:25 2% SDS in water:isopropanol and allowed to coagulate for 10 min. A control fiber was also made by preparing a solution of 0.70 g PLGA in 3.0 g DMSO and extruding a fiber through a 23 gauge needle into de-ionized water.

2) Suture placement. A total of 3 female New Zealand white rabbits (over 3 kg each) were used for this study. The test suture was removed from a sterile jar with a sterile forceps. The suture is fed through the eye of a sterile surgical needle. This creates a loop of suture attached to the eye of the needle and therefore a "double stranded suture," such as that depicted in FIGS. 1b and 1c. The rabbit is anesthetized and topical tetracaine drops are placed in the eyes of the rabbit. A sterile adhesive plastic surgical drape with a central hole is placed at the eyelid margin with the hole oriented in the area of the lid fissure. The drape adherent to the lid is pulled to retract the lower lid thus exposing the inferior conjunctival fornix. The conjunctiva is grasped with a fine tissue forceps and the needle with the attached loop of suture is passed under the conjunctiva in the inferior fornix. The needle pass is the length of the cutting part of the needle which is 10 mm. This results in placement of a 10 mm length of "double stranded suture" under the conjunctiva. The suture entering and exiting the conjunctiva is cut 2 mm from the conjunctival surface leaving a 2 mm tag of exposed sutures at the entrance and exit points. Antibiotic ointment is placed in the eyes after suture placement. FIG. 13 depicts an implanted suture in the eye of the rabbit. Each rabbit received an experimental fiber and a control fiber in opposite eyes, with the surgeon blinded to which fiber contained drug.

After the sutures were implanted, irritation was initially observe in 2 eyes but cleared after the application of a lubricant. By day two of the trial, no visible irritation was observed and the rabbits seemed healthy and behaved as they did before the surgery.

3) End Experiment—Retrieval of Sutures and Tissue

At the end of the experiment rabbits are anesthetized and topical tetracaine drops are placed in the eyes. At the end of the procedure, antibiotic ointment is placed in each eye.

Suture Removal. A sterile eyelid speculum is placed to expose the inferior fornix. Photographs of the sutures are obtained at a 1 to 1 magnification. The exposed suture tags are grasped with a fine needle holder and pulled from the conjunctiva. If the sutures are encapsulated with conjunctiva overgrowth, fine surgical scissors are used to make an incision over the sutures. Once exposed the sutures are removed with a fine needle holder. FIG. 14 depicts a "double stranded suture" that has been removed from the animal, illustrating that implantation of the sutures is reversible.

Drug Loading Determination. After the sutures were removed, their lengths were measured with calipers and they were digested with 0.15 g 1 M NaOH. Samples of the fiber that were not implanted were also digested so that the drug loading could be compared. Loading determinations were made by HPLC. Overall, for 3 animals, a decrease in fiber loading of 17%±5% was observed after 4 days, thus indicating that the sutures had delivered the drug to the animal patient.

EQUIVALENTS

Those skilled in the art will recognize, or be able to ascertain using no more than routine experimentation, numerous equivalents to the fibers and methods of use thereof described herein. Such equivalents are considered to be within the scope of this invention and are covered by the following claims.

All publications and patents cited herein are hereby incorporated by reference in their entirety.

We claim:

1. A fiber in a tubular configuration or a ribbon configuration comprising:
  a) one or more polymers;
  b) one or more cyclodextrins; and
  c) one or more therapeutic agents;
  wherein the fiber is flexible and wherein the fiber when in a tubular configuration has a diameter of about 0.1 mm to about 5 mm, and wherein the fiber when in a ribbon configuration has a thickness of about 0.1 mm to about 2 mm, and wherein the therapeutic agent is present throughout the width of the fiber.

2. The fiber of claim 1, wherein the therapeutic agent is present at a substantially uniform concentration throughout the width of the fiber.

3. The fiber of claim 1, wherein the therapeutic agent forms an inclusion complex with the cyclodextrin.

4. The fiber of claim 1, wherein the cyclodextrin and polymer are not covalently linked.

5. The fiber of claim 1, wherein the cyclodextrin and polymer are covalently linked.

6. The fiber of claim 4, further comprising a non-cyclodextrin containing polymer.

7. The fiber of claim 6, wherein the non-cyclodextrin containing polymer is poly(lactide-coglycolide) (PLGA).

8. The fiber of claim 5, wherein the cyclodextrin is incorporated in the backbone of the polymer.

9. The fiber of claim 5, wherein the cyclodextrin is borne in side chains of the polymer.

10. The fiber of claim 1, wherein the cyclodextrin is a modified cyclodextrin.

11. The fiber of claim 10, wherein the modified cyclodextrin is benzylated, acylated, or alkylated.

12. The fiber of claim 10, wherein the modified cyclodextrin is methylated cyclodextrin.

13. The fiber of claim 10, wherein the modified cyclodextrin is hydroxypropylated cyclodextrin.

14. The fiber of claim 10, wherein the modified cyclodextrin is sulfobutylether cyclodextrin.

15. The fiber of claim 1, wherein the polymer is biodegradable.

16. The fiber of claim 15, wherein the polymer is poly(lactide-coglycolide) (PLGA), polyglycolic acid (PGA), polylactic acid (PLA), polycaprolactone (PCL), polydioxanone (PDO), or a combination thereof.

17. The fiber of claim 16, wherein the polymer is PLGA.

18. The fiber of claim 1, wherein the therapeutic agent is a nucleic acid, a protein, a peptide, a small molecule, or a combination thereof.

19. The fiber of claim 18, wherein the therapeutic agent is a small molecule.

20. The fiber of claim 19, wherein the therapeutic agent is a steroid, a retinoid, a NSAID, a vitamin D3 analog, a human carbonic anhydrase inhibitor, or a combination thereof.

21. The fiber of claim 20, wherein the therapeutic agent is a steroid.

22. The fiber of claim 21, wherein the steroid is a corticosteroid.

23. The fiber of claim 21, wherein the therapeutic agent is prednisolone or dexamethasone.

24. The fiber of claim 18, wherein the therapeutic agent is a protein.

25. The fiber of claim 24, wherein the therapeutic agent is a neurotrophic factor.

26. The fiber of claim 25, wherein the therapeutic agent is a nerve growth factor.

27. The fiber of claim 1, wherein the therapeutic agent is an anti-cancer agent, an antibiotic agent, an anti-inflammatory agent, an immunosuppressant, an antiviral agent, an anti-proliferative agent, an antimicrobial agent, a nerve growth inducing agent, or a combination thereof.

28. The fiber of claim 27, wherein the therapeutic agent is an antibiotic agent or an anti-microbial agent.

29. The fiber of claim 28, wherein the therapeutic agent is chlorhexidine, metronidazole, minocycline, tetracycline, triclosan, ciprofloxacin or tobramycin.

30. The fiber of claim 29, wherein the therapeutic agent is a nerve growth inducing agent.

31. The fiber of claim 30, wherein the therapeutic agent is sabeluzole or inosine.

32. The fiber of claim 1, further comprising one or more adjuvants.

33. The fiber of claim 1, wherein the therapeutic agent is covalently linked to the polymer.

34. The fiber of claim 33, wherein the therapeutic agent is covalently linked to the polymer by one or more linking moieties.

35. The fiber of claim 34, wherein one or more linking moieties are cleaved under physiological conditions.

36. The fiber of claim 1, further comprising one or more coatings.

37. The fiber of claim 36, wherein the coating comprises one or more therapeutic agents or adjuvants.

38. The fiber of claim 1, wherein the fiber comprises one or more bulbs along the length of the fiber.

39. The fiber of claim 38, wherein at least one bulb comprises one or more therapeutic agents.

40. The fiber of claim 1, wherein the fiber gradually releases the therapeutic agent over a period of time after implantation in a patient.

41. The fiber of claim 1, wherein the fiber releases an initial surge of the therapeutic agent after implantation in a patient.

42. The fiber of claim 1, wherein the fiber releases a gradually increasing amount of the therapeutic agent over a period of time after implantation in a patient.

43. The fiber of claim 1, wherein the fiber includes a ribbon configuration portion.

44. The fiber of claim 1, wherein the fiber includes a tube configuration portion.

45. The fiber of claim 44, wherein the fiber includes a lumen.

46. The fiber of claim 45, wherein the lumen contains a medium that includes one or more auxiliary therapeutic agents.

47. The fiber of claim 46, wherein one or more auxiliary therapeutic agents is a nerve growth inducing agent.

48. A thread comprising one or more fibers of claim 1.

49. The thread of claim 48, wherein the thread is a monofilament.

50. The thread of claim 48, wherein the thread is a polyfilament.

51. The thread of claim 48, wherein the thread is braided.

52. The thread of claim 48, further comprising one or more fibers that are non-bioabsorbable.

53. The thread of claim 48, wherein at least one additional fiber comprises one or more therapeutic agents or adjuvants.

54. The thread of claim 48, further comprising one or more layers or plies.

55. The thread of claim 48, wherein the thread is implanted in a targeted tissue of a patient.

56. The thread of claim 55, wherein the tissue is the periodontal tissue.

57. The thread of claim 56, wherein the therapeutic agent is an antibiotic or antimicrobial agent.

58. The thread of claim 57, wherein the therapeutic agent is chlorhexidine, metronidazole, minocycline, triclosan, or tetracycline.

59. A suture comprising one or more threads of claim 48.

60. The suture of claim 59, wherein the suture comprises two or more threads.

61. The suture of claim 59, wherein two or more threads comprise different therapeutic agents.

62. The suture of claim 59, wherein the suture is attached to a needle.

63. The suture of claim 59, wherein the suture is implanted or tied to a targeted tissue of a patient.

64. The suture of claim 63, wherein the tissue is ocular tissue.

65. The suture of claim 64, wherein the tissue is the sub-conjunctival space.

66. The suture of claim 64, wherein the tissue is the conjunctival formix.

67. A method for delivering one or more therapeutic agents to a targeted tissue in a patient, comprising introducing the fiber of claim 1 to the targeted tissue.

68. The method of claim 67, wherein the fiber includes a ribbon configuration portion.

69. The method of claim 67, wherein the fiber includes a tube configuration portion.

70. The method of claim 67, wherein the tissue is ocular tissue.

71. The method of claim 70, wherein the tissue is the sub-conjunctival space.

72. The method of claim 70, wherein the tissue is the conjunctival formix.

73. The method of claim 67, wherein the tissue is periodontal tissue.

74. The method of claim 67, wherein the introduction of the fiber is reversible.

75. The method of claim 67, wherein the therapeutic agent treats cancer.

76. The method of claim 67, wherein the therapeutic agent is an antibiotic agent or an anti-microbial agent.

77. The method of claim 76, wherein the therapeutic agent is chlorhexidine, metronidazole, minocycline, tetracycline, triclosan, ciprofloxacin or tobramycin.

78. The method of claim 67, wherein the therapeutic agent treats an ocular disease or disorder.

79. The method of claim 78, wherein the ocular disease or disorder is corneal ulcer, uveitis, scleritis, glaucoma, or vernal conjunctivitis.

80. The method of claim 78, wherein the therapeutic agent is ciprofloxacin, 5-fluorouracil, tobramycin, dexamethasone, prednisolone, or combinations thereof.

81. The method of claim 67, wherein the therapeutic agent treats periodontitis.

82. The method of claim 81, wherein the therapeutic agent is chlorhexidine, metronidazole, minocycline, triclosan, or tetracycline.

83. The method of claim 67, wherein the tissue is nerve tissue.

84. The method of claim 67, wherein the therapeutic agent is a neurotrophic factor.

85. The method of claim 84, wherein the therapeutic agent induces nerve growth.

86. A method for the treatment of periodontitis, comprising administering to a patient the fiber of claim 1.

87. The method of claim 86, wherein the therapeutic agent is an antibiotic agent.

88. The method of claim 86, additionally comprising treating the patient with scaling.

89. The method of claim 86, additionally comprising treating the patient with root planing.

90. A method for the treatment of nerve damage comprising administering to a patient the fiber of claim 1.

91. The method of claim 90, wherein the therapeutic agent is a neurotrophic agent.

92. The method of claim 90, wherein the fiber includes a tube configuration.

93. A method for the preparation of a drug-eluting fiber of claim 1 comprising:
   a) dissolving one or more polymers and one or more cyclodextrin-therapeutic agent inclusion complexes in a solvent to give a polymer solution; and
   b) exposing the polymer solution to a coagulation fluid to prepare a drug-eluting fiber.

94. The method of claim 93, wherein exposing the polymer solution to a coagulation fluid comprises extruding the polymer solution into a coagulation fluid.

95. The method of claim 94, wherein exposing the polymer solution to a coagulation fluid comprises dip-coating.

96. The method of claim 93, wherein the polymer solution is homogeneous.

97. The method of claim 93, wherein one or more polymers is PLGA.

98. The method of claim 93, wherein the cyclodextrin is a modified cyclodextrin.

99. The method of claim 93, wherein, the therapeutic agent is nucleic acid, a protein, a peptide, a small molecule, or a combination thereof.

100. The method of claim 93, wherein the solvent is DMF.

101. The method of claim 93, wherein the solvent is DMSO.

102. The method of claim 93, wherein the coagulation fluid is water, an alcohol, or a combination thereof.

103. The method of claim 102, wherein the alcohol is isopropanol.

104. The method of claim 103, wherein the coagulation fluid is a water:isopropanol mixture.

105. The method of claim 93, wherein the coagulation fluid includes a surfactant.

106. The method of claim 105, wherein the surfactant is an anionic surfactant.

107. The method of claim 106, wherein the surfactant is sodium dodecylsulfate.

108. The thread of claim of claim 48, wherein the thread includes one or more biodegradable sections not including a therapeutic agent.

109. The thread of claim 108, wherein the biodegradable section not including a therapeutic agent is at a tail end of the thread.

110. The thread of claim 1, wherein the fiber is in the form a tubular structure and has a diameter of about 0.4 mm to about 1 mm.

* * * * *

UNITED STATES PATENT AND TRADEMARK OFFICE
CERTIFICATE OF CORRECTION

PATENT NO. : 8,128,954 B2
APPLICATION NO. : 11/148011
DATED : March 6, 2012
INVENTOR(S) : Davis et al.

It is certified that error appears in the above-identified patent and that said Letters Patent is hereby corrected as shown below:

In the Claims:

Column 45, Claim 30, line 4, delete "claim 29" and insert --claim 27--.

Column 46, Claim 72, line 25, delete "formix." and insert --fornix.--.

Signed and Sealed this
First Day of May, 2012

David J. Kappos
*Director of the United States Patent and Trademark Office*